US008849387B2

(12) United States Patent
Gilbert et al.

(10) Patent No.: US 8,849,387 B2
(45) Date of Patent: Sep. 30, 2014

(54) LOW-POWER, COMPACT, RESILIENT SYSTEM AND METHOD FOR PHYSIOLOGICAL MONITORING

(71) Applicants: Barry Gilbert, Rochester, MN (US); Clifton Haider, Rochester, MN (US); Christopher Felton, Rochester, MN (US); Daniel Schwab, Mantorville, MN (US)

(72) Inventors: Barry Gilbert, Rochester, MN (US); Clifton Haider, Rochester, MN (US); Christopher Felton, Rochester, MN (US); Daniel Schwab, Mantorville, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/906,316

(22) Filed: May 30, 2013

(65) Prior Publication Data
US 2014/0012143 A1    Jan. 9, 2014

Related U.S. Application Data

(60) Provisional application No. 61/653,296, filed on May 30, 2012.

(51) Int. Cl.
| | | |
|---|---|---|
| *A61B 5/0404* | (2006.01) | |
| *A61B 5/11* | (2006.01) | |
| *A61B 5/0245* | (2006.01) | |
| *A61B 5/0205* | (2006.01) | |
| *A61B 5/024* | (2006.01) | |
| *A61B 5/0456* | (2006.01) | |

(52) U.S. Cl.
CPC ....... *A61B 5/0205* (2013.01); *A61B 2562/0219* (2013.01); *A61B 2562/182* (2013.01); *A61B 5/1118* (2013.01); *A61B 5/0245* (2013.01); *A61B 5/1101* (2013.01); *A61B 5/02438* (2013.01); *A61B 5/02405* (2013.01); *A61B 5/0456* (2013.01)
USPC ............ 600/520; 600/509; 600/521; 600/523

(58) Field of Classification Search
USPC .................................. 600/509, 520, 521, 523
See application file for complete search history.

(56) References Cited

U.S. PATENT DOCUMENTS

| | | | |
|---|---|---|---|
| 6,253,097 B1 | 6/2001 | Aronow et al. | |
| 6,711,425 B1 | 3/2004 | Reuss | |

(Continued)

FOREIGN PATENT DOCUMENTS

WO        03014714 A1     2/2003

OTHER PUBLICATIONS

Daniel J. Sebald, "Motivation of Pulse Oximetry", Design of PulseOximeters pp. 13-14.

(Continued)

*Primary Examiner* — Christopher D Koharski
*Assistant Examiner* — Michael Carey
(74) *Attorney, Agent, or Firm* — Yakov Sidorin; Quarles & Brady LLP

(57) ABSTRACT

A monitor of a physiological parameter of subject under test to which the monitor is attached, in operation. The monitor includes a set of accelerometers operating in different ranges of acceleration and a physiological sensor. The physiological sensor may include an ECG circuit producing an output data characterizing the subject as a function of a degree of motion and/or reorientation of the monitor or an oximeter device. The process of monitoring includes a determination of R-wave of the subject.

15 Claims, 27 Drawing Sheets

(56) References Cited

U.S. PATENT DOCUMENTS

| | | | |
|---|---|---|---|
| 7,206,621 | B2 | 4/2007 | Aoyagi et al. |
| 7,349,726 | B2 | 3/2008 | Casciani et al. |
| 8,172,761 | B1 * | 5/2012 | Rulkov et al. .......... 600/503 |
| 2005/0240087 | A1 * | 10/2005 | Keenan et al. .......... 600/301 |

OTHER PUBLICATIONS

K. Ashoka Reddy, et al., "A Novel Calibration-Free Method of Measurement of Oxygen Saturation in Arterial Blood", IEEE Transaction on Instrumentation and Measurement, vol 58, No. 5, May 2009, pp. 1699-1705.

Takuo Aoyagi, et al., "Multiwavelength Pulse Oximetry: Theory for the Future", International Anesthesia Research Society, vol. 105, No. 6, Dec. 2007 pp. S53-.

Leslie Brown, "A New Instrument for the Simultaneous Measurement of Total Hemoglobin, % Oxyhemoglobin, % Carboxyhemoglobin, % Methemoglobin, and Oxygen Content in Whole Blood", IEEE Transactions on Biomedical Engineering, vol. BME-27, No. 3, Mar. 1980, pp. 132-138.

Paul D. Mannheimer, "Wavelength Selection for Low-Saturation Pulse Oximetry", IEEE Transactions on Biomedical Engineering, vol. 44, No. 3, Mar. 1997, pp. 148-158.

* cited by examiner

LOW-POWER, COMPACT, RESILIENT SYSTEM AND METHOD FOR PHYSIOLOGICAL MONITORING

CROSS-REFERENCE TO RELATED APPLICATIONS

This patent application claims benefit of and priority from the U.S. Provisional Patent Application No. 61/653,296 filed on May 30, 2012 and titled "Activity Monitor". The disclosure of the above-mentioned provisional patent application is incorporated by reference herein in its entirety.

TECHNICAL FIELD

The present application relates to activity monitors and, in particular, to a monitor enabled to record data representing physiological parameters of a wearer of the monitor.

BACKGROUND

There are several circumstances in which it may be desirable to monitor a person's physical activity. Athletes, the elderly, patients, mountaineers, are but a few examples of persons who may benefit or desire monitoring of their physical activity levels. An activity monitor may include sensors for monitoring physical movement of a person such as accelerometers, magnetometers, pressure sensors, altimeters, velocity sensors, angular velocity sensors, and gyroscopes, for example. An activity monitor may also include a sensor for monitoring physiological parameters, such as temperature, heart rate, blood pressure, electrocardiogram (ECG), and/or enabling other sensing functions.

SUMMARY

Embodiments of the invention provide a method for characterization of physiology of the subject under test, the method including a step of acquiring, with a controller of the monitor device, a first output from a motion sensor of the monitor device, the first output representing orientation and motion of the monitor unit in multiple ranges of acceleration, the monitor unit having a port in electrical communication with the subject. The method further includes acquiring, with the controller, a second output from a physiological sensor of the monitor device, the second output representing a physiological parameter of the subject. The method additionally includes sending data derived from the acquired at least one of the first and second outputs to a data-logging unit of the monitor device, the data-logging unit including tangible non-transitory storage medium.

Embodiments of the invention additionally provide an article of manufacture that contains a monitor unit including, on a single integrated board, (i) a motion sensor enabled to collect first data representing orientation and motions of the article in multiple ranges of acceleration, the motion sensor generating a first output, (ii) a physiological sensor enabled to collect second data representing a physiological parameter and generating a second output, and (iii) a data-logging unit including tangible non-transitory storage medium. The article of manufacture additionally includes a controller in operable communication with the motion sensor and the physiological sensor, the controller receiving the first and second outputs and routing data associated with at least one of the first and second outputs to said data-logging unit. The article of manufacture optionally contains an electrically-conducting lead electrically connected to a port of the monitor unit.

In one example, a body-worn physiological monitor and data logger includes motion and electrocardiogram (ECG) sensing functions. In another example, the activity monitor may include one or more features to "ruggedize" it for use in physically demanding, environmentally harsh operating conditions. In another example, the activity monitor may also include extraction of Heart Rate (HR) and Heart Rate Variability (HRV) during ECG data processing.

BRIEF DESCRIPTION OF THE DRAWINGS

The details of the invention will become apparent from a description provided below in conjunction with the drawings, of which

DETAILED DESCRIPTION

The Biomedical Platform-Activity Monitor, or BP-AM, hereinafter referred to as a monitor, is a body-worn physiological monitor and data logger that is configured to implement motion and electrocardiogram (ECG) sensing functions. The BP-AM monitor is structured according to a "platform" concept, which means that the monitor employs a base, common set of components (the platform) to which other components or sub-systems enabled to implement auxiliary sensing functions can be added. Specifically, a common/core set of components and circuit functions such as the microcontroller (uC), NAND flash main memory, timing crystals (including a high precision time stamp crystal), universal serial bus (USB) communication port and other support circuits such as voltage regulators, switches and light emitting diode (LED) indicators are being used. This suite of parts forms the platform to which other functions are added, such as sensors and radio frequency (RF) communication circuits.

An embodiment of the monitor contains three different accelerometers to provide end users with choices of operational modes of the monitor (for example, a motion measurement range, resolution, and other features such as "wake up on motion event" capabilities, to name just a few). The ECG circuit of the monitor can be configured as either a two- or three-electrode circuit and can be sampled at user-selected rates to allow tailoring for different heart monitoring applications. In addition to various sensing functions, an embodiment of the monitor contains a precision time clock and provisions multiple battery types.

Figure 1:
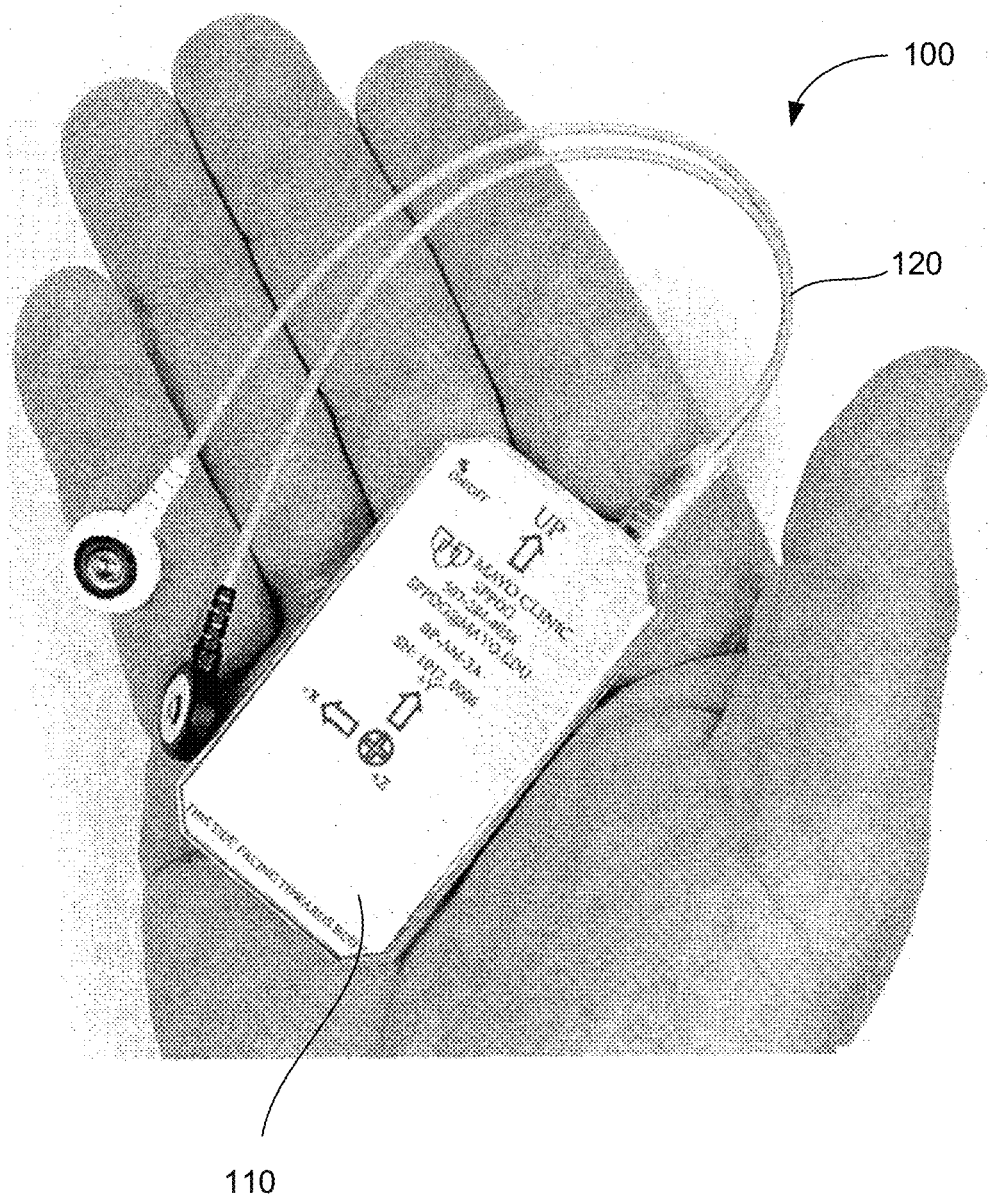
FIG. 1 is a perspective view of an embodiment of the invention.

In reference to FIG. 1, the monitor 100 (model BP-AM-3A) is miniaturized and housed in a small, thin (for patient comfort) and rugged aluminum case 110 with dimensions of 70.2 mm by 38.9 mm by 8.9 mm, weighing only about 46.9 grams with leads 120 (and 39.5 grams without leads 120). The embodiment 100 is configured to acquire, with a 12-bit sampling resolution, about 400 data samples per second for ECG and about 10 samples per second for each accelerometer axis. The power supply for the embodiment 100 includes a 750 mAh battery with a nominal running time of about two weeks. The version of the Biomedical Platform that the embodiment 100 employs was designed with a number of special features to "ruggedize" it for use in physically demanding, environmentally harsh operating conditions.

Figures 2A, 2B:
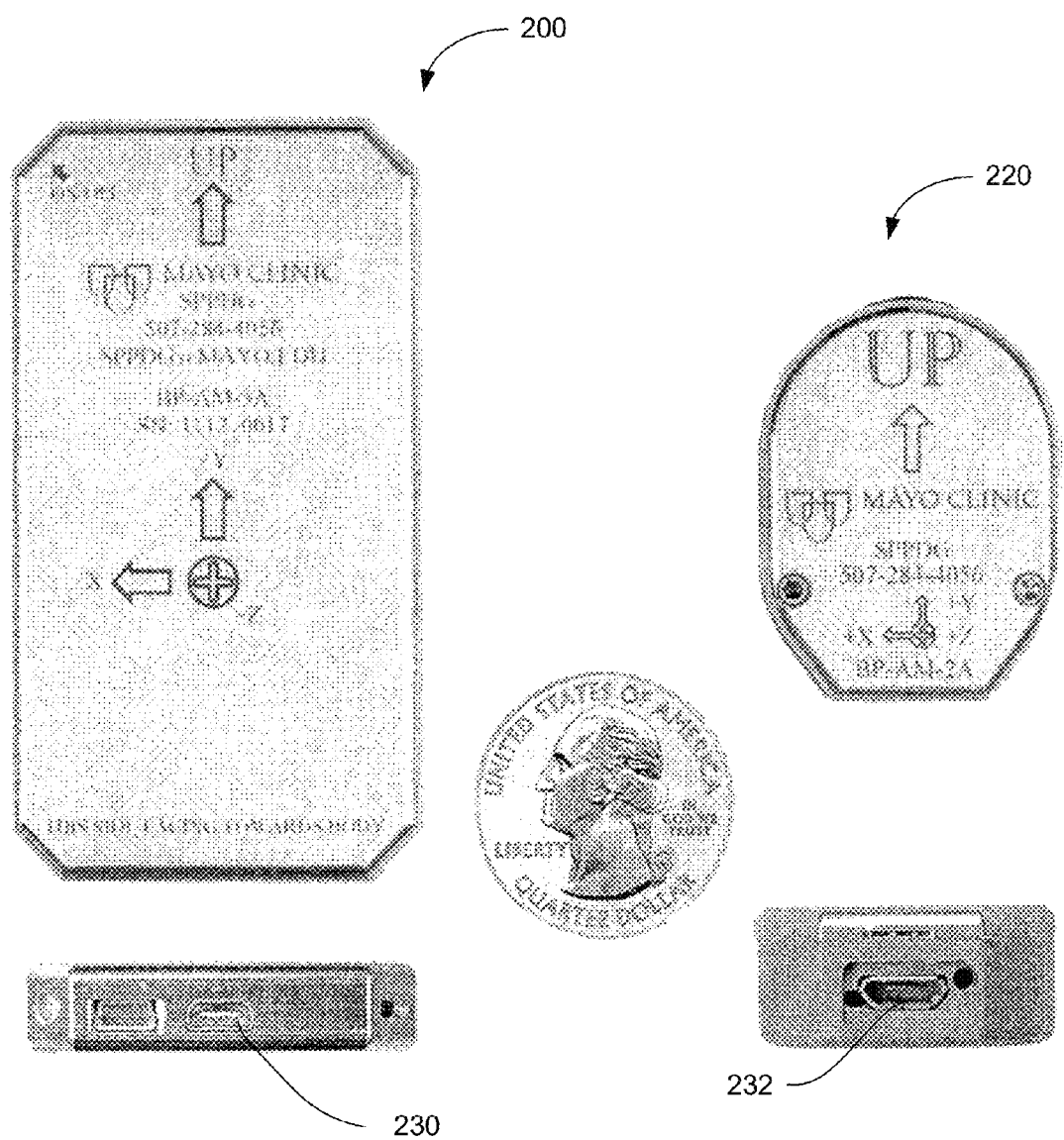
FIGS. 2A and 2B are views of related embodiments of the invention.

The related embodiments 200 and 220 are shown in FIGS. 2A and 2B, respectively. The body of the embodiment 260, for example, is dimensioned to be 27.8 mm by 36.7 mm by 12.6 mm, weighs 21.5 grams without leads, and is driven by a 500 mAh battery for a nominal running time of about two weeks.

Data logging times are configuration-dependent but can range from a week to several months. Data are easily downloaded from the embodiments of the monitor through the use of a cable that plugs connects a port 230, 232 of the monitor and a universal serial bus (USB) port on a personal computer (PC). Post processing of downloaded data provides information for the end users.

Figure 3:
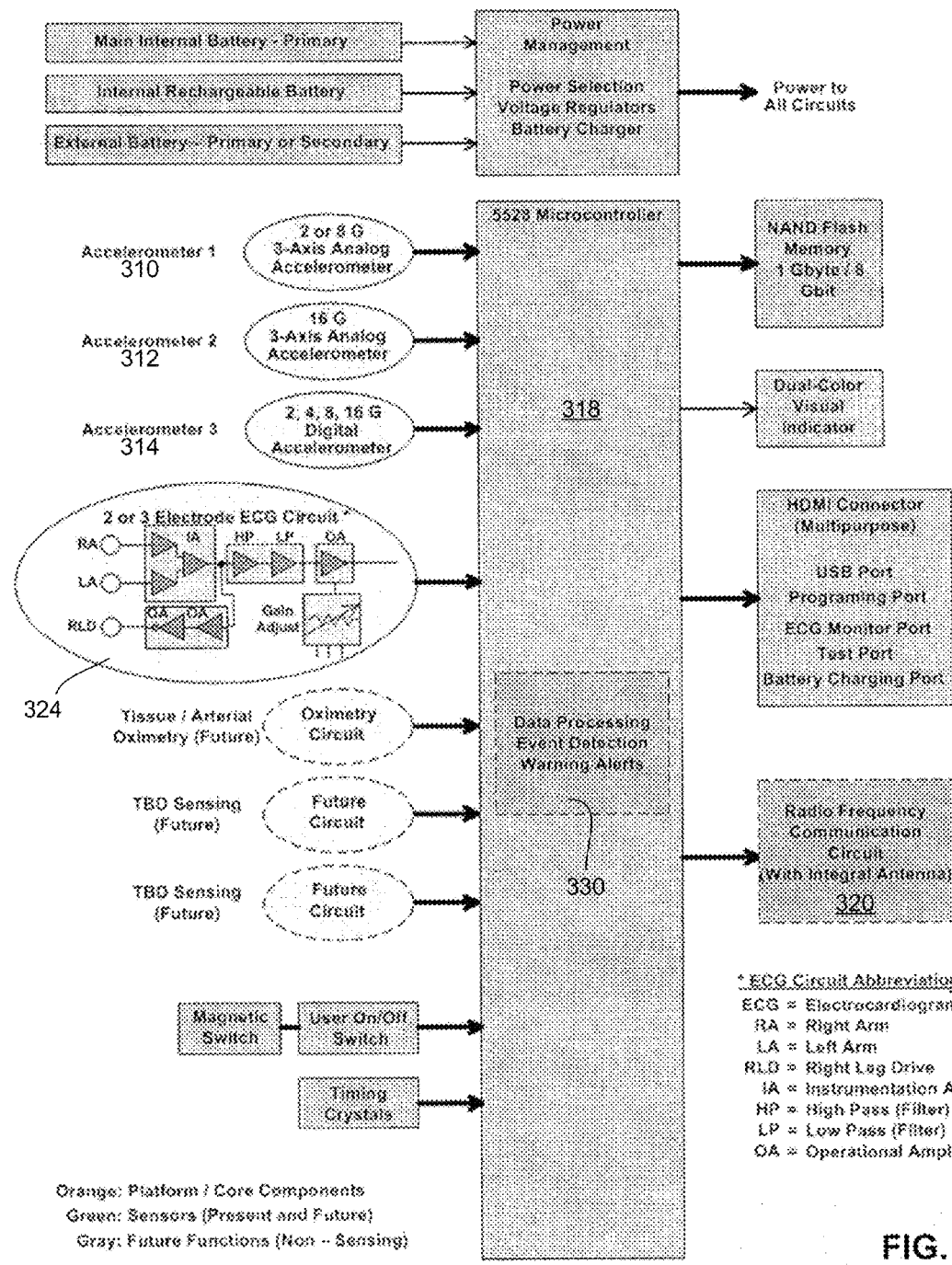
FIG. 3 is a high-level block diagram of the electronic circuitry of the embodiment of FIG. 1.

FIG. 3 is a high-level block diagram of the electronic circuitry of the embodiment 100 of FIG. 1. The development path for this platform initially concentrates on data logging using multiple sensors, to be followed by wireless data transmission and communication. The data-processing unit operating in real time, configured to provide user-alerts of various types, is also within the scope of the invention.

In further reference to FIGS. 1, 2A, 2B, and 3, the embodiment of the monitor contains a set of three accelerometers 310, 312, 314 in order to enable a sensing capability and provide end users with a choice of measurement ranges.

The first accelerometer, 310, is a selectable dual range 2 or 8 G component; one range or the other may be used, but not both at the same time. The higher sensitivity 2 G range is intended for measurements of fine motion such as, for example, Parkinson's disease tremors, or the monitoring of breathing (when a monitor is juxtaposed with the chest of the user). The 8 G range would be applicable for general motion measurements and has been proven suitable even for epileptic seizure measurements. The 16 G accelerometer 312 is suitable for the measurements of the large amplitude motion such as, for example, monitoring of the motions of extreme athletes or the most extreme seizure monitoring. The 16 G accelerometer can be used by itself or in combination with the 2/8 G accelerometer, thereby providing the capability to capture both large amplitude motion events (16 G) and finer motion events (2 G) at the same time. In addition to different ranges of measurements, different sample rates such as 10, 20, 50, 100, 200 or 400 samples per second (SPS) and sampling amplitude resolution values can be selected by the user for each of the accelerometers. The accelerometers 310 and 312 provide an analog output voltage that is digitized with up to 12 bits of resolution by the integral analog-to-digital (ADC) within the uC. For example, users could select 8, 10, or 12 bits of amplitude resolution at the different rates just described, with individual rates and resolution tailored for each accelerometer if so desired.

The third accelerometer 314 is a quad-range component that had selectable ranges of 2, 4, 8, and 16 G. This accelerometer has an integral 10-bit ADC and can support selectable sampling rates from 1 SPS to 5,000 SPS. (This accelerometer is referred to as the digital accelerometer, because of its digital serial interface to the uC.) The accelerometer 314 has a built-in element enabling wake-up-on-event/inertia/orientation operational capabilities with programmable levels. Accordingly, the accelerometer 314 is enabled for use for monitoring of improper posture, improper orientation, and/or detection of a fall event. According to an embodiment of the invention, the accelerometer 314 is used either independently or in operable combination with at least one of the other two accelerometers 310 and 312.

Example

Optionally, the digital accelerometer 314 could be configured to operate at a low sample rate such as 10 SPS. Upon an event such as a seizure that exceeds the value of the threshold with which a microcontroller 318 is preprogrammed, the wake-on-event interrupt would have the uC activate one of the other accelerometers (310, 312) to provide high rate and resolution sampling for a defined time during and after the seizure event. In addition, an alert signal could be sent, as an output, through the RF communication circuit 320 (described below) to a medical monitoring station or medical facility. Temperature sensing is also integrally provided with this accelerometer and there are provisions to add additional sensing functions to the external analog inputs on this accelerometer component.

The ability to monitor the ECG of a subject/patient is the second primary sensing function. In further reference to FIG. 3, the ECG circuit 324 includes multiple analog gain stages. The first stage is a differential input instrumentation amplifier with a nominal gain coefficient of 10, followed by a 0.5 Hz high pass filter (characterized by a local gain coefficient of 1) and then a 200 Hz low pass filter with a gain coefficient of 100. The final stage is an operational amplifier with manually configured fixed gains or an end-user-controlled programmable gain feature. Default gain level for this output stage is one; therefore, the total gain level of the amplifier chain is about 1,000,000.

Figure 4:
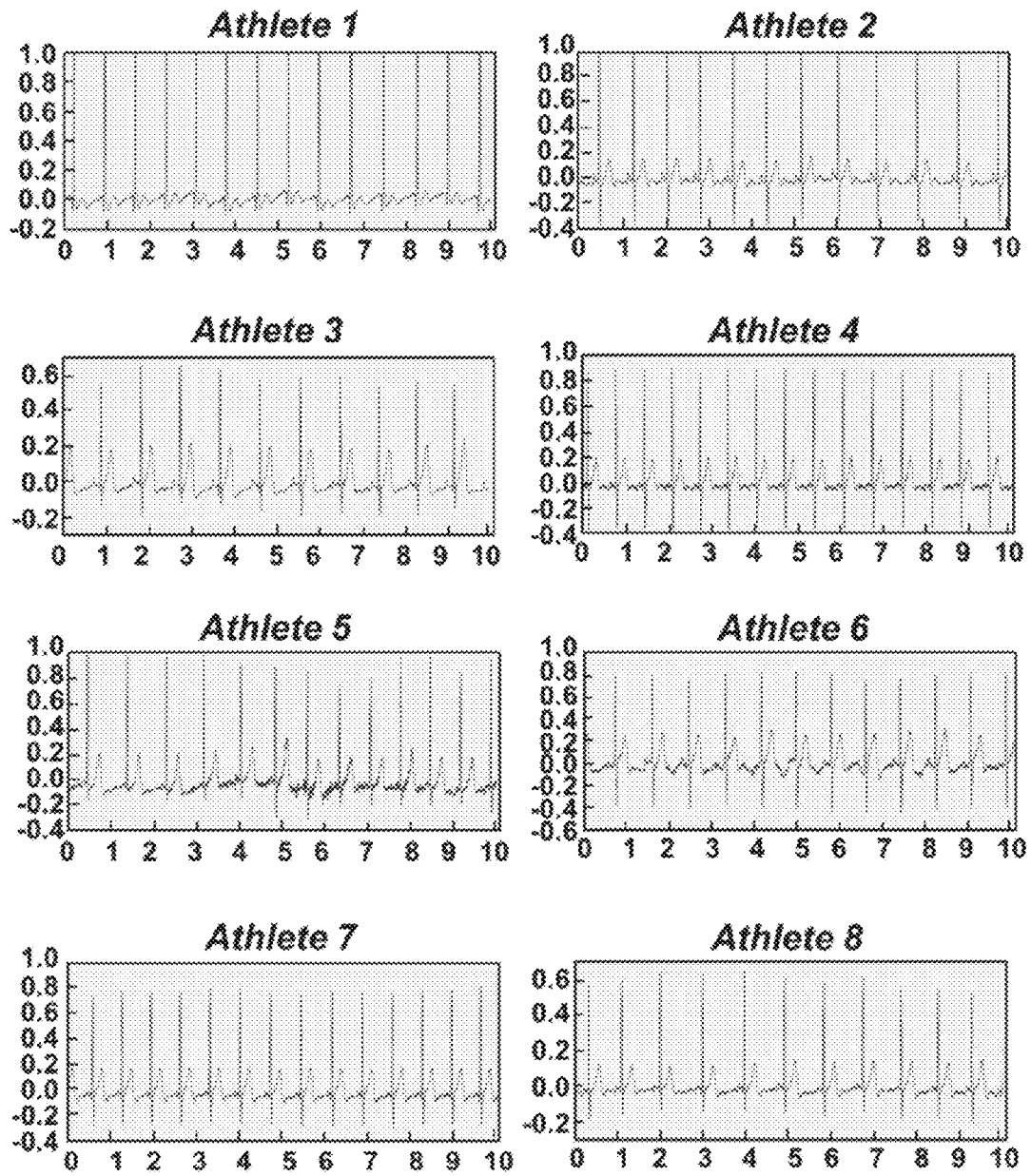
FIG. 4 is a diagram providing an empirical example of waveforms acquired from eight different test subjects using the embodiment of FIG. 1.
Figure 5A:
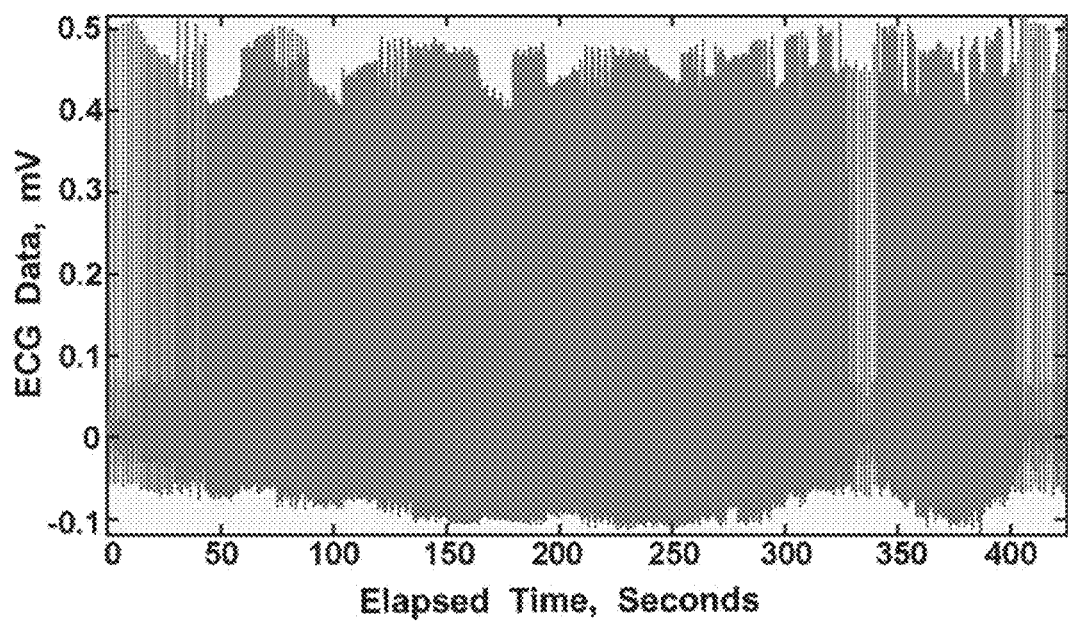
FIGS. 5A and 5B are plots depicting results from a variable rate electrocardiographic test of the subject effectuated with the embodiment of FIG. 1.
Figure 5B:
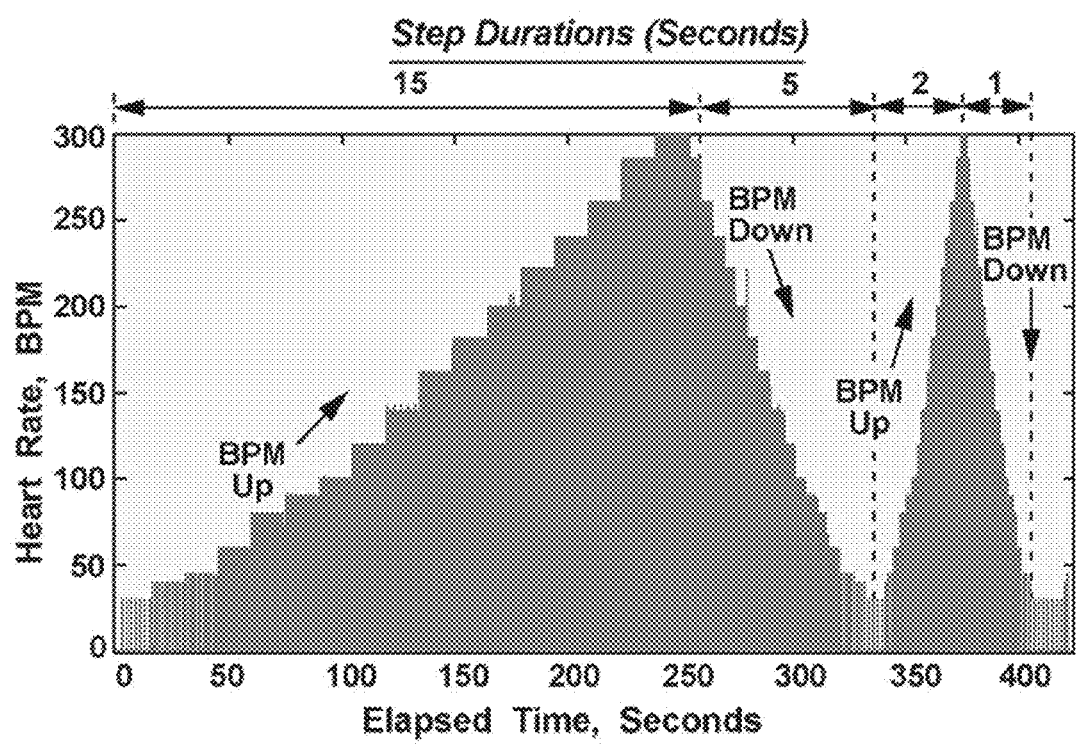

In one embodiment, the ECG circuit 324 can be used in a two-electrode configuration, which is the lowest power circuit configuration with a nominal current draw of 100 uA. The nominal power of the ECG circuit 324 is 0.3 mW (the ECG circuit uses a regulated 2.8 volt supply). This circuit relies on the nominal 100 dB common mode rejection feature of the instrumentation amplifier to cancel out externally induced noise and common mode signals such as those produced by muscle movements. The circuit 324 is intended to be used for the lowest power and longest run time applications with the primary purpose of heart rate (HR) and heart rate variability (HRV) measurements. The following diagrams illustrate the operation of an embodiment of the invention. FIG. 4 is a diagram providing an empirical example of waveforms acquired (at the 400 samples per second sampling rate of the ECG channel and a 10-samples-per-second rate for the 8 G accelerometer 314) from eight different test subjects using the embodiment 100 employing the two-electrode circuit 324. No accelerometer data are displayed. FIGS. 5A and 5B are plots depicting the results from a variable rate ECG test. An ECG simulator was used to vary the heart rate at specific intervals spanning 15 seconds to 1 second as shown in FIG. 5B. This ECG simulator data were acquired with the two-electrode version of the circuit 324 of FIG. 3, stored, downloaded and then processed with a computer processor specifically programmed to determine the heart rate as a function of time.

Referring again to FIG. 3, a higher-fidelity three-electrode configuration of the ECG circuit 324 includes an additional dual operational amplifier to provide an active cancellation signal path back to the body, referred to as the Right Leg drive (RLD) or Wilson Central Terminal (WCT) function. This implementation of the circuit 324 provides better rejection of noise and other common mode artifacts at the expense of slightly increased power consumption. Here, the nominal current draw is 135 uA, while the nominal power consumption is 4 mW. Such circuit can be used in the HR and HRV monitoring applications, but will provide better quality ECG signals for other heart-monitoring needs as well.

Either the two- or three-electrode version of the ECG circuit 324 are configured to enable gain adjustments made either manually or via programming by the user. The sample rate can also be varied under user control in a similar manner to the accelerometers; sample rates can range from 10 SPS to 400 SPS or even higher. In addition, with the envisioned auxiliary firmware (sub-system 330) configured to provide data monitoring and limited analysis functions (in a power efficient manner), automatic adjustments could be made to gain and sample rates to insure that the signal of interest is being properly acquired.

The embodiment of the monitor is structured to incorporate additional sub-systems enabling auxiliary sensing capabilities such as, for example, a sub-system for tissue/arterial oximetry sensing enabled with the use of advanced and low power optical components, or a sub-system for measurement of respiration, body temperature, galvanic skin response, and oximetry characteristics, to name just a few.

Figure 6:
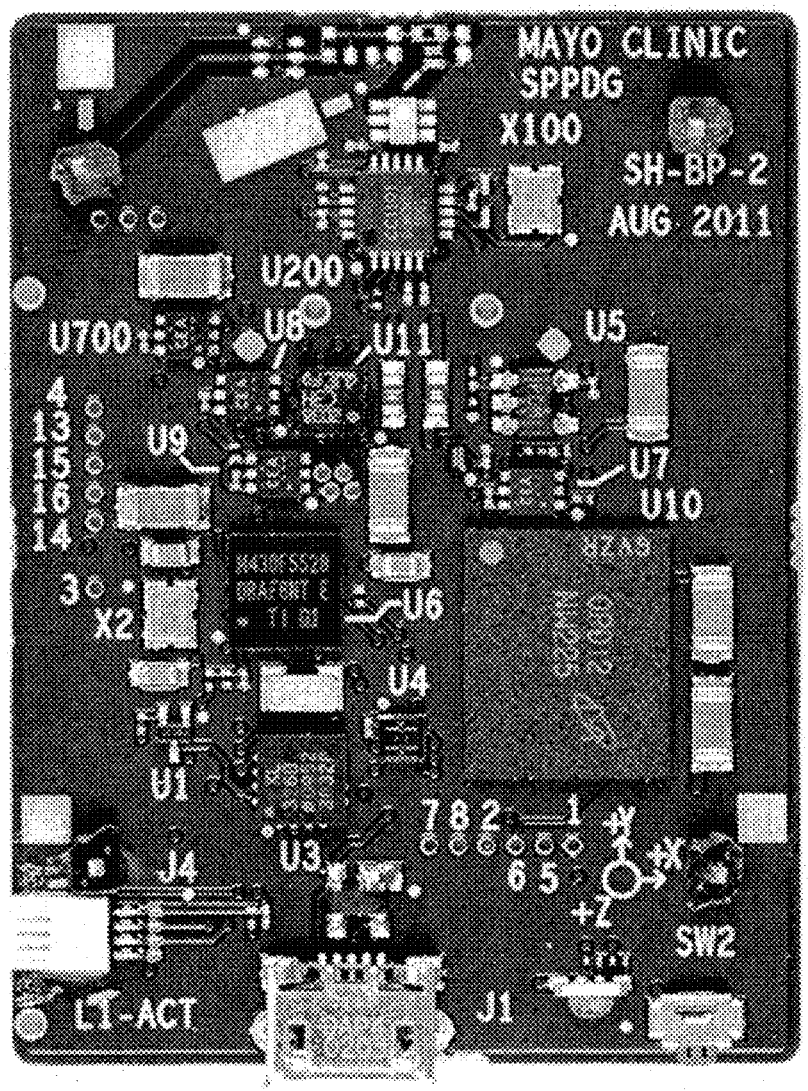
FIG. 6 is a diagram showing the RF circuit integrated with the embodiment of FIG. 2B.
Figure 7:
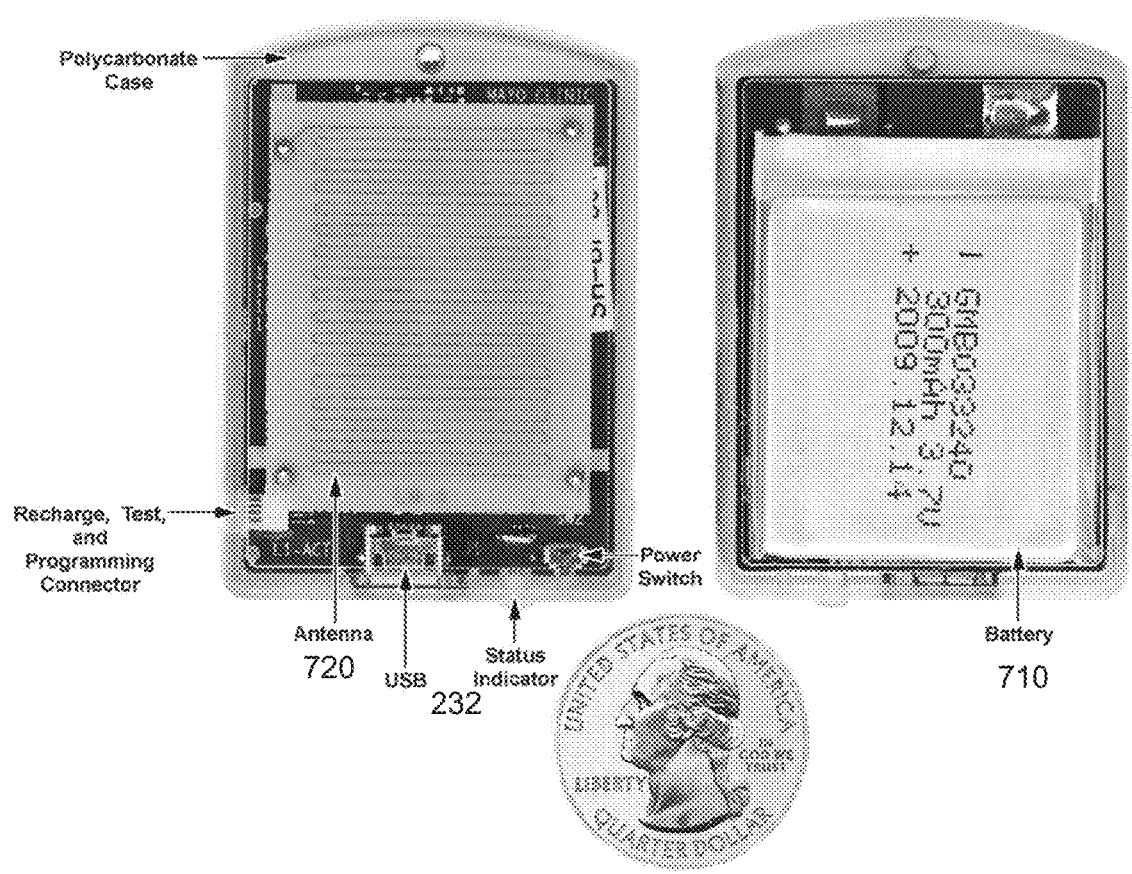
FIG. 7 shows a board of a short-haul circuit in association with a battery and antenna.

The RF communication circuit function block 320 has been developed and successfully mated and integrated with the embodiments of the monitor. FIG. 6 is a diagram showing the RF circuit 320 integrated with the embodiment 220 of FIG. 2B. This integrated system is identified as the short-haul circuit (SH-BP-2) design. The SH-BP-2 board with battery 710 and antenna 720 is shown in FIG. 7.

Figure 8:
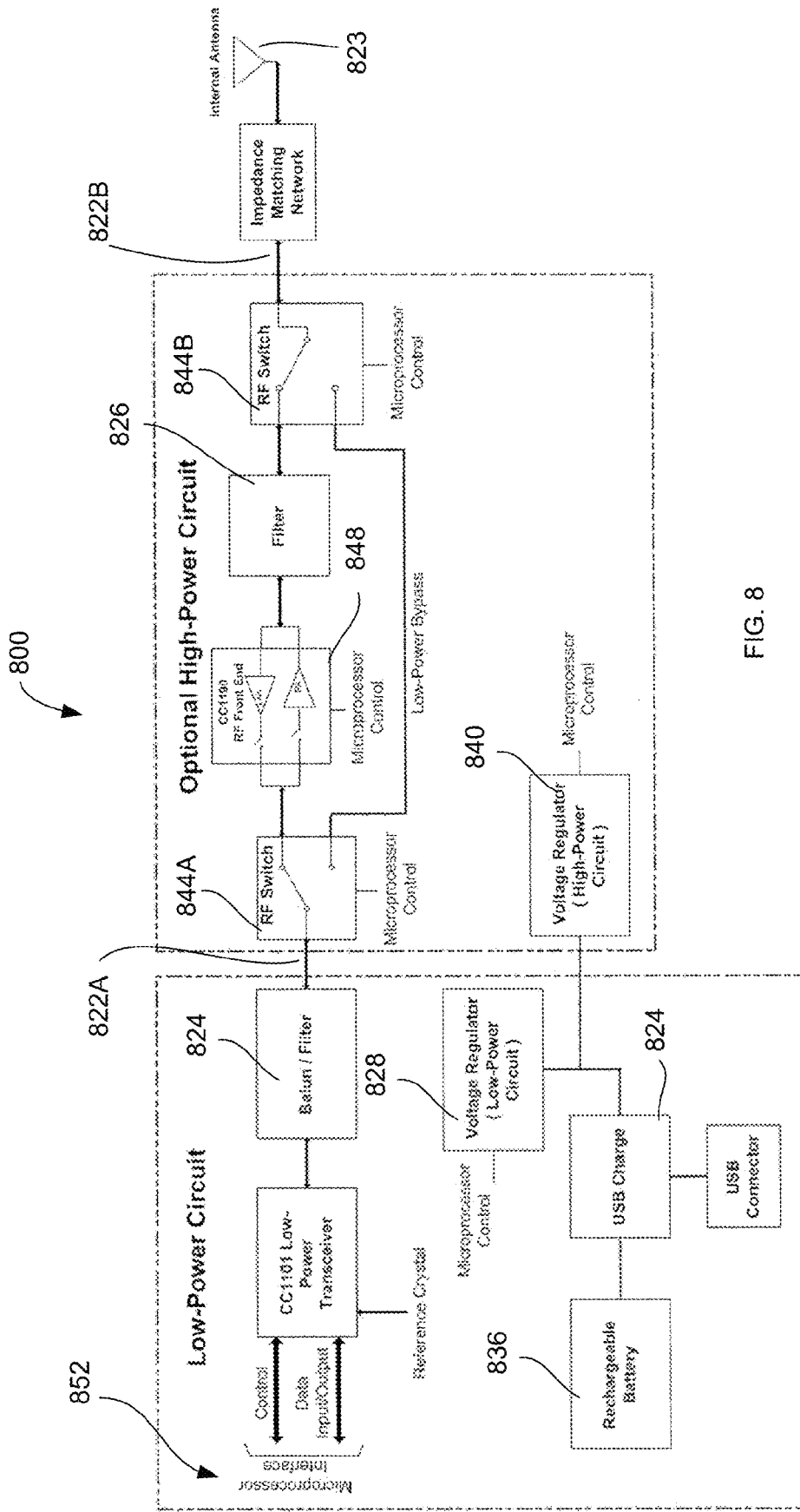
FIG. 8 is a block-diagram of the short-haul circuit of FIG. 7.

The block diagram of the SH-BP-2 system 800 is shown in FIG. 8. Here, the RF communication circuit includes the low-power circuit 810 that is optionally complemented with a high-power circuit 820, receiving as an input 822A a signal from the circuit 810 and transmitting an output 822B towards the internal antenna 823. As shown, the short-haul wireless link is based on a 902 MHz to 928 MHz industrial, scientific, and medical (ISM) band low power radio frequency (RF) transceiver integrated circuit. Additional components and sub-circuits include a ceramic balun/filter 824, a discrete component output filter 826, a dedicated voltage regulator 828, USB charge circuit 832, and a rechargeable battery 836. An antenna matching circuit with electrostatic discharge (ESD) protection is also included which connects to an internal antenna mounted above one side of the printed circuit board. An optional high power circuit 820 includes the a higher-current regulator 840, two RF switches 844A, 844B, and an RF front-end 848, which in operation adds (i) a low noise amplifier (LNA) to improve receive sensitivity, and (ii) a power amplifier (PA) for additional transmit power.

During operation, the transceiver configuration registers are initially loaded from the same microprocessor 852 that is used for the data logger. Digital data are then sent to and received from the transceiver over the same serial peripheral interface (SPI) used for the register load. When the detectable level of the received signal falls below a predetermined level, as reported by a built-in transceiver function, the RF front-end circuit regulator 848 is enabled and the front-end LNA and PA circuits are incrementally powered up and switched into the signal path as needed. When the RF front-end circuit 848 is not required, however, the RF switches 844A, 844B route receive and transmit signals around the circuit 848 and the high current voltage regulator 840, which supplies power to this circuit only, remains in the "off" state.

Example

Figure 9:
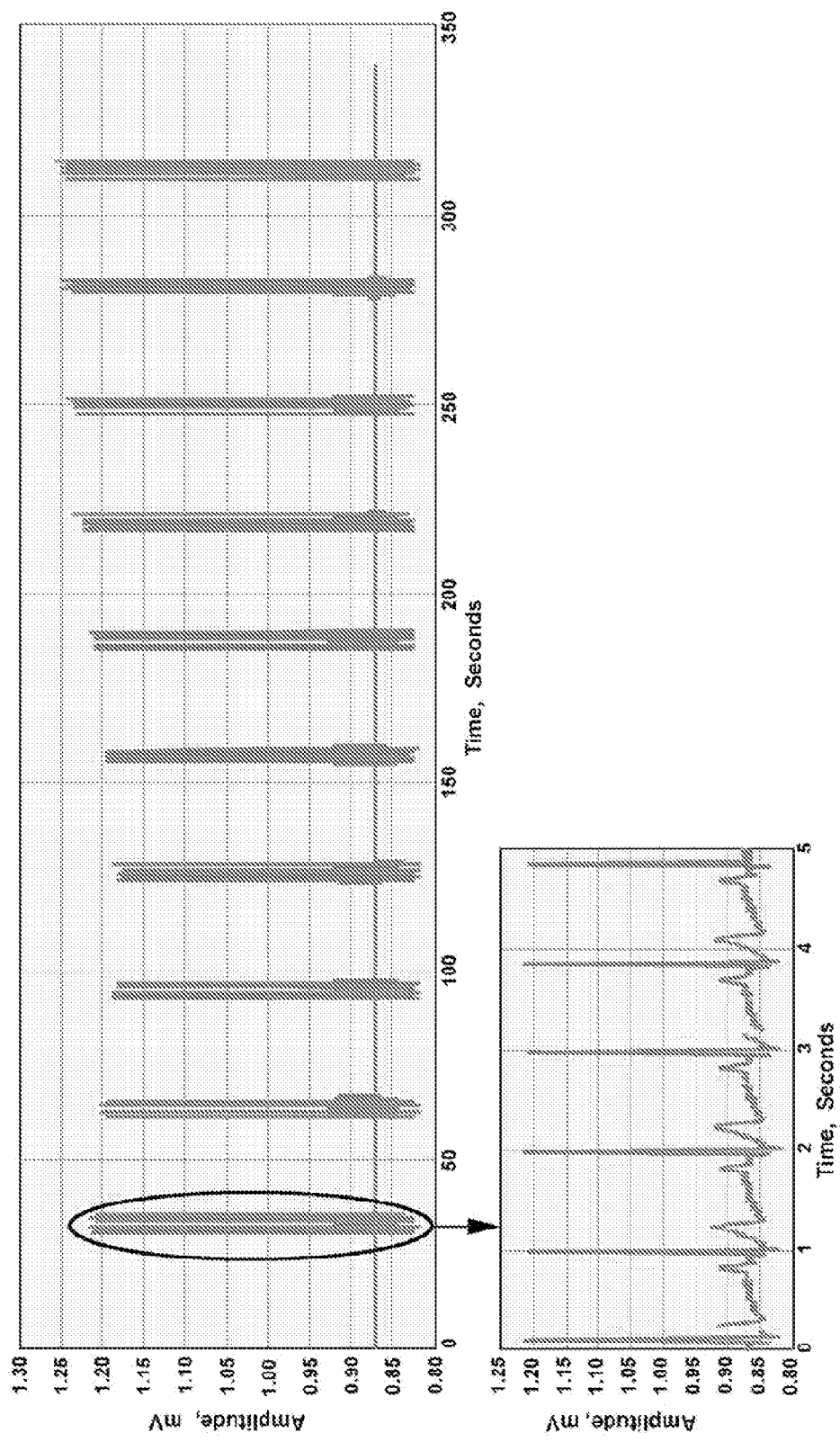
FIG. 9 includes plots of data representing simulated heart rate and acquired with an embodiment including the short-haul circuit of FIG. 7.
Figure 10:
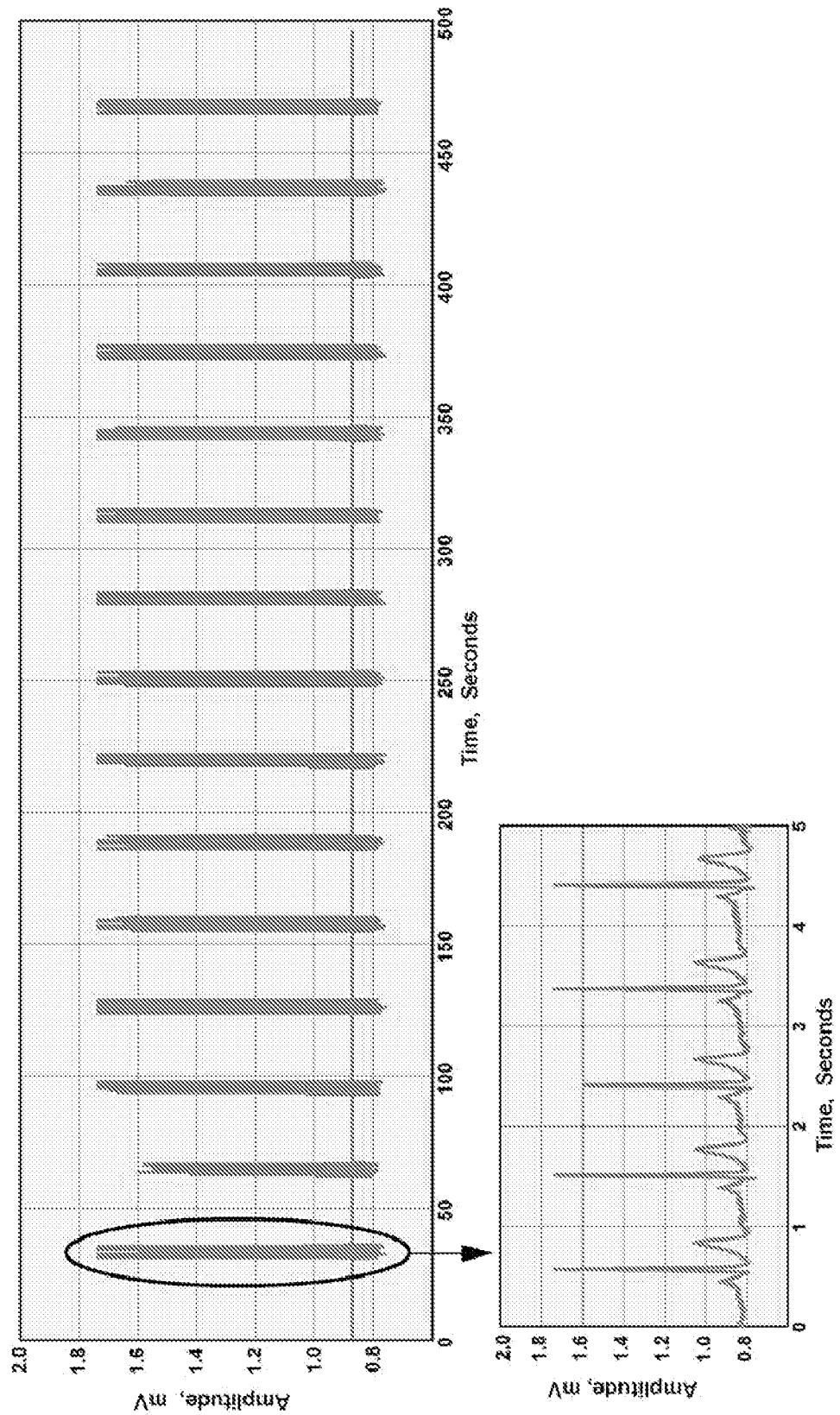
FIG. 10 includes plots of data representing heart rate empirically acquired from a subject under test with an embodiment including the short-haul circuit of FIG. 7.

The two-electrode version of ECG circuit 324 of FIG. 3 was mated with the short-haul circuit 800 of FIG. 8 to demonstrate the operability of the system with respect to the acquisition of an ECG waveform, storing the acquired ECG waveform, and transmission of the portions of the ECG signal to an end user (a medical center, for example). The result of this demonstration is shown in FIG. 9, which depicts the data representing heart rate of a subject as received over a cable modem from a Fluke MPS450 Simulator connected to the ECG breadboard and the short-haul biomedical platform of an embodiment of the invention. The ECG stimulator was used as a signal source. All of the ECG data were stored on the SH-BP-2 unit. Five-second portions of the ECG signal were transmitted from the SH-BP-2 to a nearby gateway, and then onto a monitoring computer. FIG. 10 shows plots representing the results from a similar test. Here, however, the ECG data was recorded by a monitor unit juxtaposed with normal subject volunteer and transmitted from a private residence, in the same manner as for the demonstration using the ECG simulator described in reference to FIG. 9. Accordingly, the complete path of ECG signal acquisition, data storage, and transmission of periodic ECG portions (snippets) has been practically demonstrated.

Figure 11:
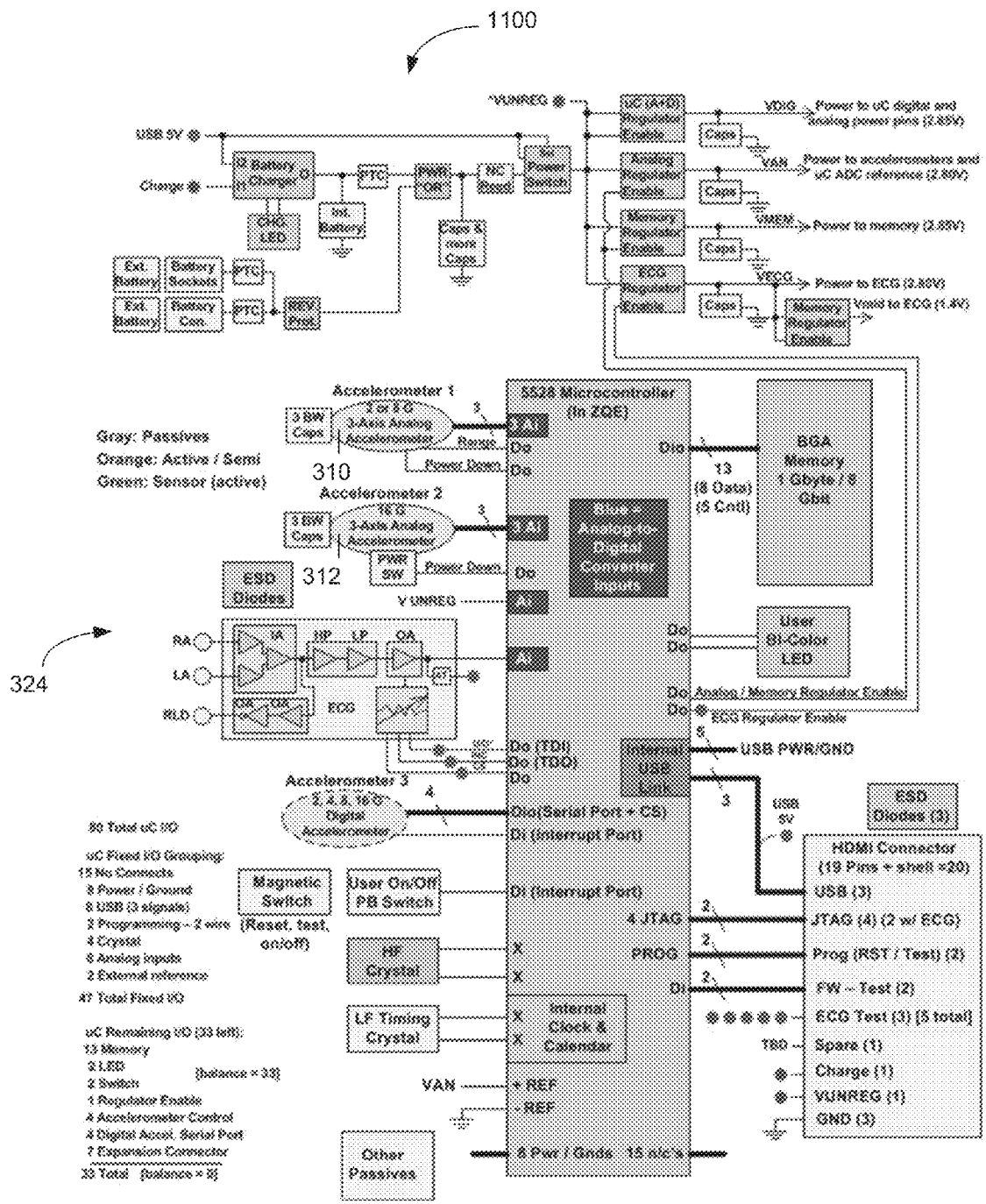
FIG. 11 is a diagram of block scheme of a related embodiment.

FIG. 11 is a diagram of block scheme of a related embodiment 1100 of the invention, showing (as compared to FIG. 3) additional structural elements of the system. Included in the platform core group of components is the uC. This uC performs an internal timekeeping function with the use of an external crystal (characterized by tolerance of +/−3 part per million or +/−3 PPM, which is much more time-stable than the commonly available +/−20 and +/−10 PPM crystals). This timing function is used as not only a data logging time stamp, but provisions can be made to wake the unit up at a precise time to begin a sampling sequence (as discussed below). The timed activation feature enables the unit to turn on at a precise time and without an input for the user, for example on a day of expected beginning of exploitation. The monitor is worn by (on) the user and then automatically turned off at the end of the expected study period, thereby reducing the size of data file that does not include any data acquired prior to or after the period of monitor-wearing (such as, for example, during the time of mailing the monitor to and from the user).

In one embodiment, a magnetic switch is used to activate on the monitor on arrival or at time schedule for the beginning of exploitation. For example, the material used for packing the monitor for mailing optionally contains a magnet that maintains the magnetic switch in its "off" position. Once the unit is removed from the package and thus separated from the magnet, the unit will start and continue to run until it is returned to the package, where the magnet will turn it off, yielding a simple, foolproof way to control activation and deactivation with no end-user knowledge required. This approach also accommodates shipping delays and end-user manual "turning it on and off" procedural errors.

Figure 12:
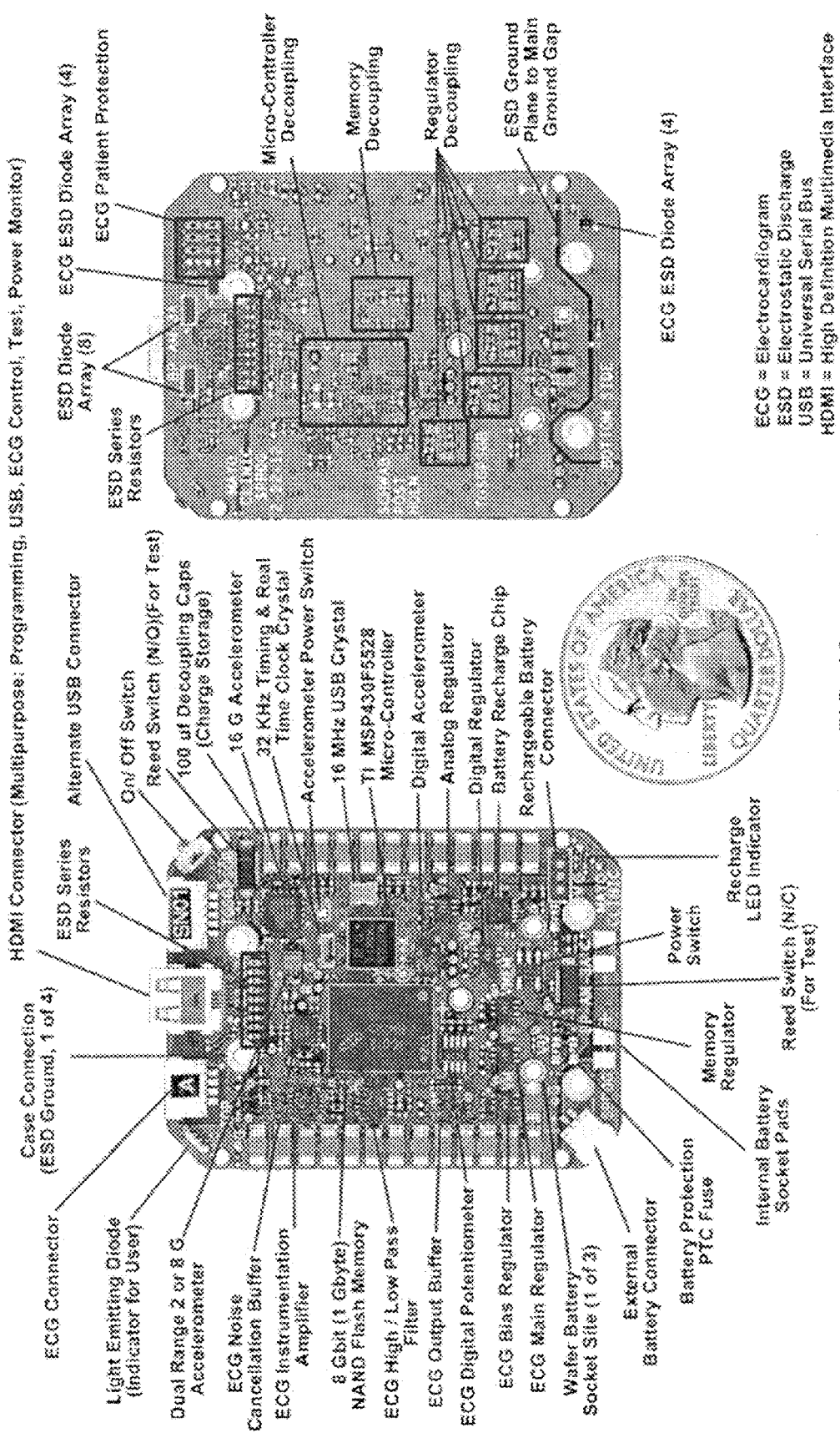
FIG. 12 shows an example of a circuit board implemented according to a related embodiment of the invention.

Another example of the BP-AM-3A circuit board, depicted in FIG. 12, is 36 mm [1.42 Inches] wide, 48 mm [1.89 Inches] high and 1.0 mm [0.039 Inches] thick. The board cross section contains eight ½ Ounce [0.016 mm/0.65 mils] copper metal layers, and seven FR4 [IT180] 0.1 mm [4 mil]/0.127 [4.8 mil] thick dielectric layers, and 716 total drilled holes, the smallest of which are 0.25 mm (10 mils) in diameter. The board is populated with a total of 363 components, 30 of which are active/semiconductors, while the remaining 333 are passives. The largest components have been placed on the top surface of the board and are identified in the left side of the Figure. The right side of FIG. 12 shows the bottom view of the board, which contains the smaller and thinner components. Many components are tightly spaced in order to minimize distance between them and thus the overall in-path inductance. This minimal inductance is critical in supply decoupling paths to minimize overall system noise. Additional details of the board design, physical layout, and components are described elsewhere.

Figure 13:
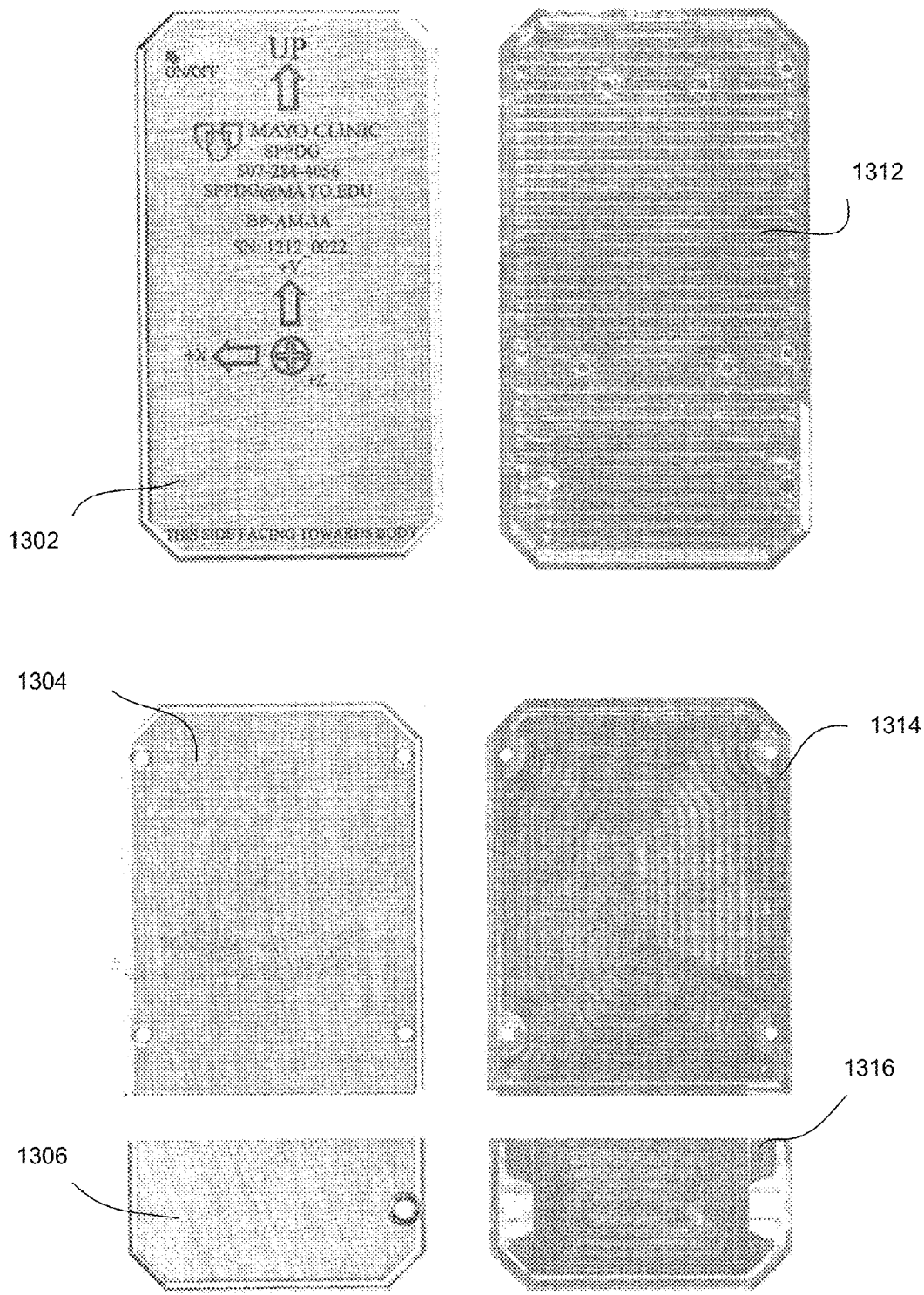
FIG. 13 includes front and back views of components of housing used with an embodiment of the invention.

The circuit board of FIG. 12 is encapsulated in aluminum housing, the three metal components of which with the outside surfaces 1302, 1304, 1306 and inside surfaces 1312, 1314, 1316 are shown in FIG. 13.

Figure 14:
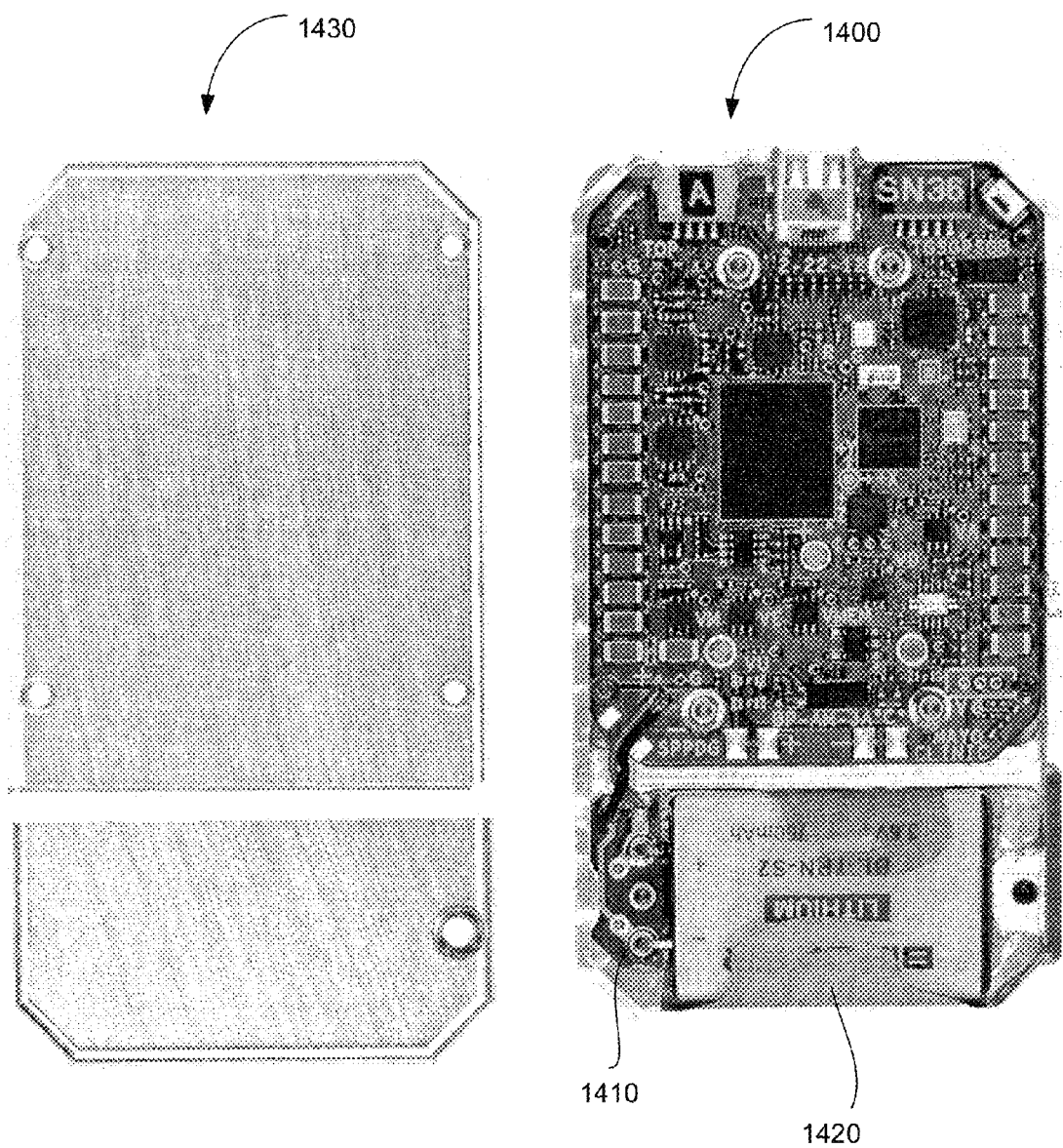
FIG. 14 shows an assembly of the main board including a small battery socket board and an installed battery.
Figure 15:
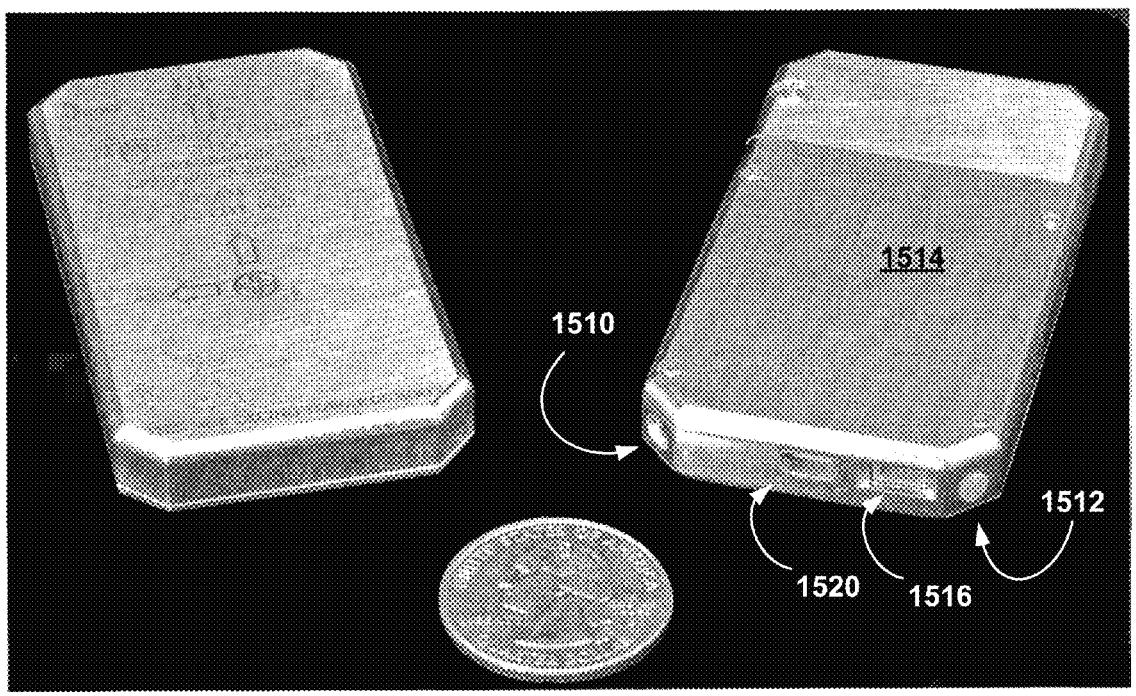
FIG. 15 provides view(s) of the assembly illustrating the connector interfaces, switch, and light emitting diode (LED) operational indicator.

An assembly of the main board 1400, including a small battery socket board 1410 and an installed battery 1420, is depicted in FIG. 14. A separate compartment and associated cover 1430 for the circuit board are shown on the left. The assembled case illustrating the connector interfaces, switch, and light emitting diode (LED) operational indicator is presented in FIG. 15. The housing case 1504 that hosts the monitor unit and the battery and auxiliary components has a thin profile to provide the best end-user comfort. The switch 1510 (in the recessed pocket near the lower left corner of the article shown on the right) is recessed to prevent inadvertent starting and stopping. The LED indicator is disposed under the translucent dome 1512 in the right corner. The ECG connector 1516, located adjacent to the LED indicator, can support a maximum of four leads. The connector 1520 near the center is a 19 pin micro High Definition Multimedia Interface (HDMI) connector that enables at least one of the following operations: USB data download and device configuration, microcontroller programming, ECG circuit monitor and gain adjustment, battery charging and, lastly, unit diagnostics.

Figure 16:
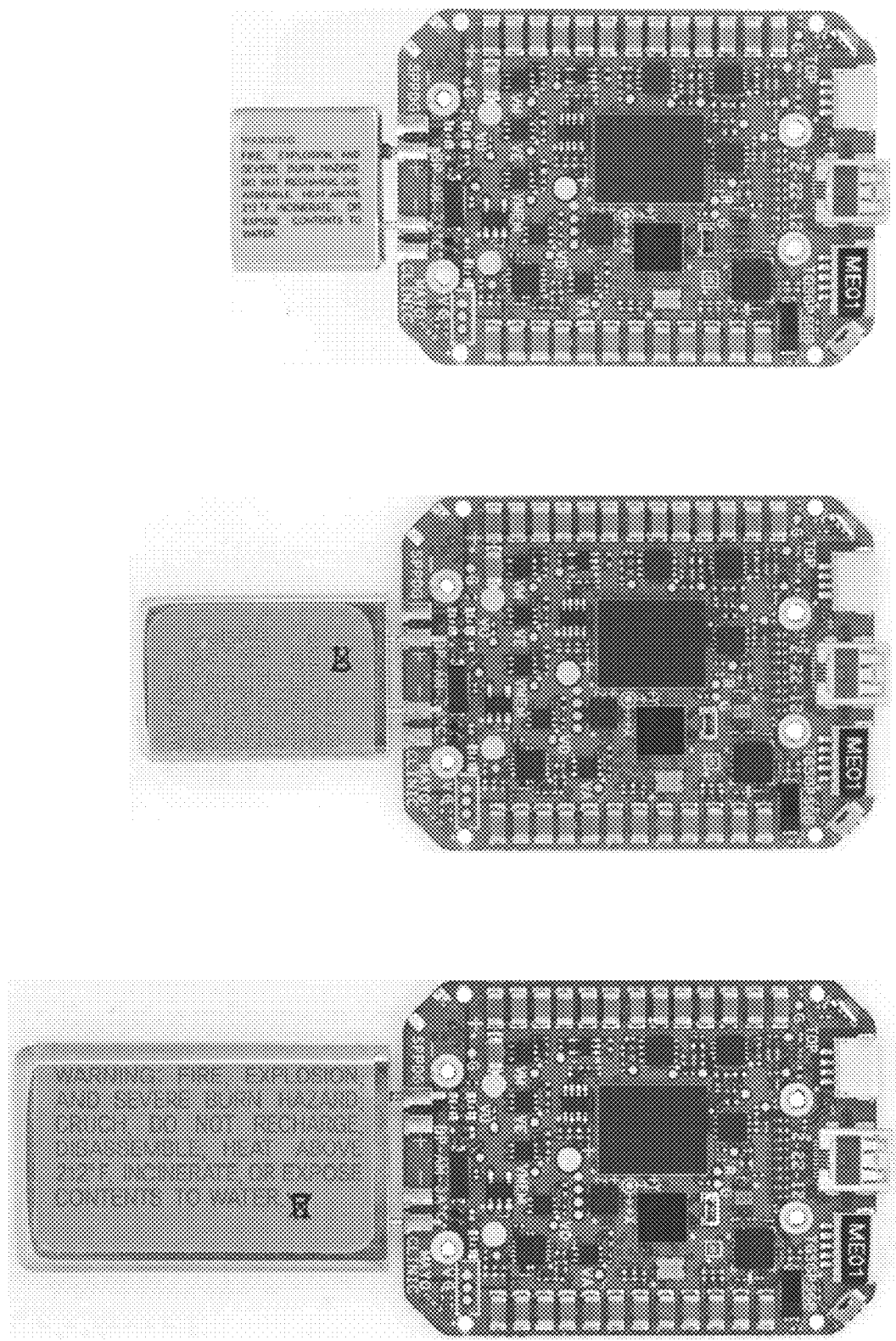
FIG. 16 provides view of batteries for use with an embodiment of the invention by means of direct coupling between a battery and the circuit board of the invention.
Figure 17:
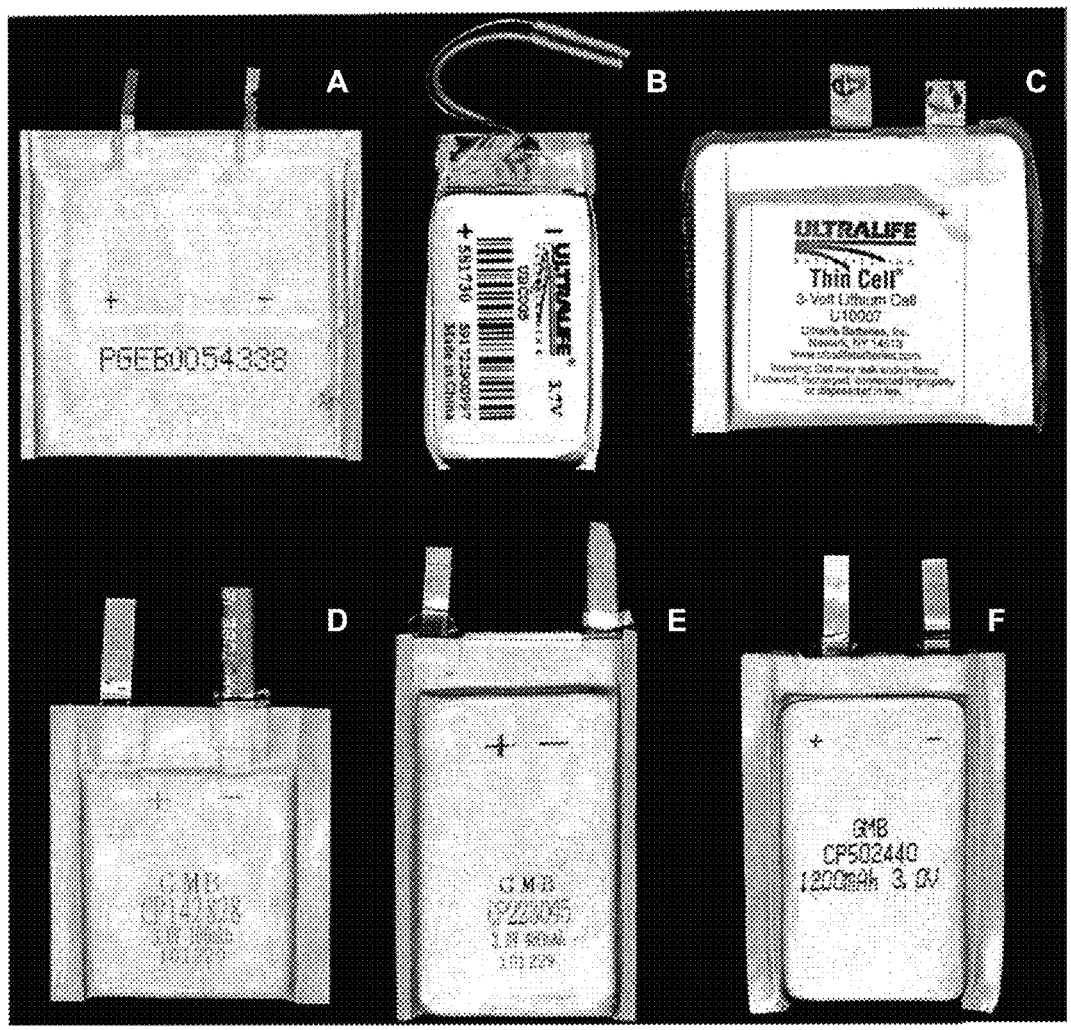
FIG. 17 provides views of auxiliary electrical batteries.
Figure 18:
FIG. 18 is view of a case for use with an embodiment of the invention.

In addition to the board and battery packaging described above, provisions have been made to allow the circuit board to be used with other batteries of different sizes and shapes, thereby enabling different run times and case packaging options to meet various end-user and or patient needs. For shorter data acquisition times of a few days or less, a smaller battery could be used, resulting in a smaller case and most importantly, an even more conformable unit for the patient. For longer run times, higher sampling rates and maximum number of active sensors, a larger battery may be required. FIG. 16 illustrates three batteries that can be plugged directly into the edge of the circuit board. These batteries have capacities of 400, 750 and 1600 mAh. In addition to the plug-in battery provisions, there are options to use several different types of thin batteries. These thin batteries can be placed to the side, or on top (or bottom), of the PCB. FIG. 17 illustrates six different batteries with capacities ranging from 45 mAH to 1200 mAh. At least some of the batteries may be rechargeable and can be used either inside the case or externally. FIG. 18 shows a small case that can be used with the existing board and the four thinnest batteries (A, C, D, E) of FIG. 17.

Figure 19:
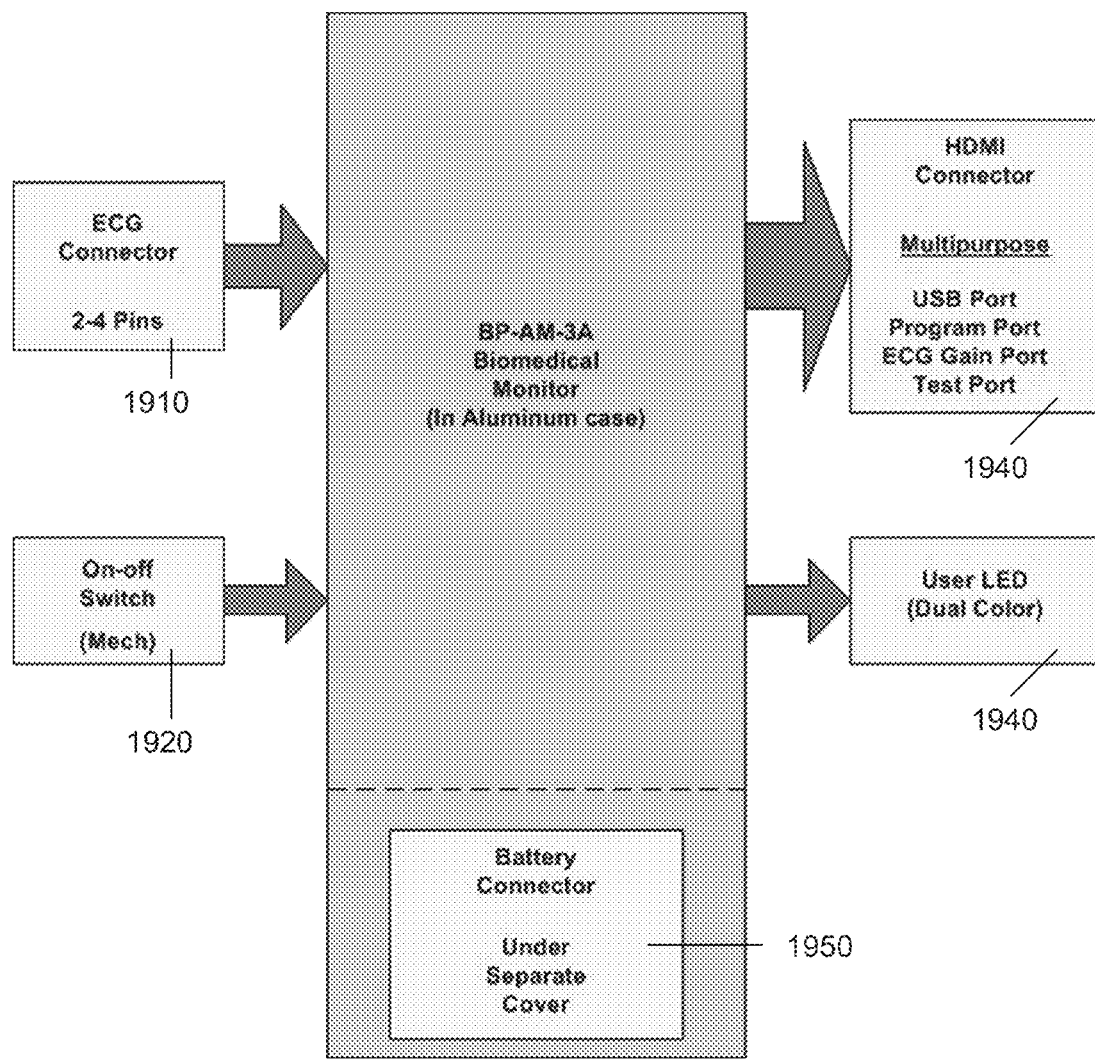
FIG. 19 a diagram depicting the five interface points of an embodiment of the invention for an end user.

Even though there are many physical configuration choices and end-user configuration options, the device is relatively simple to use. FIG. 19 is a depiction of the five interface points for the end users. On the left is the connector for the ECG leads 1910 and the user on/off switch 1920. On the right are the multipurpose connector 1930 and the LED indicator 1940. Shown at the bottom and integrated into the case is the access to the battery 1950. Therefore from the end-user point of view the device is an easy to use, highly configurable, small and comfortable data logger. Once the data is logged there are three remaining steps: offloading the data, processing the data and providing information to the clinician and or patient. These capabilities are described next.

Software Residing on the Host PC.

To facilitate sensor sample data download via the USB port on the BP-AM-3A, a computer program product has been developed, and stored on a tangible, non-transitory computer-readable storage medium, which product contains at least one program code that, when loaded on a programmable microprocessor, enables the microprocessor to communicate with an embodiment of the monitor and effectuate configuring sensors for operation and polling/sampling the sensors;

reporting the amount of memory consumed on the BP-AM by the data acquired from a sensor;

reporting the serial number, model name and firmware code revision of the embodiment of the invention;

reporting on any device errors and resolving those errors starting and stopping sampling of the sensors, a function duplicating the button on the monitor unit.

The developed computer program product provides a simple interface that would support users with different areas of responsibility. Some users may only need to execute the basic operations of starting and stopping sampling, as well as downloading data. Other more sophisticated users may be involved in sensor configuration. A third, even more sophisticated class of user may need to use specialized data communication features.

Figure 20:
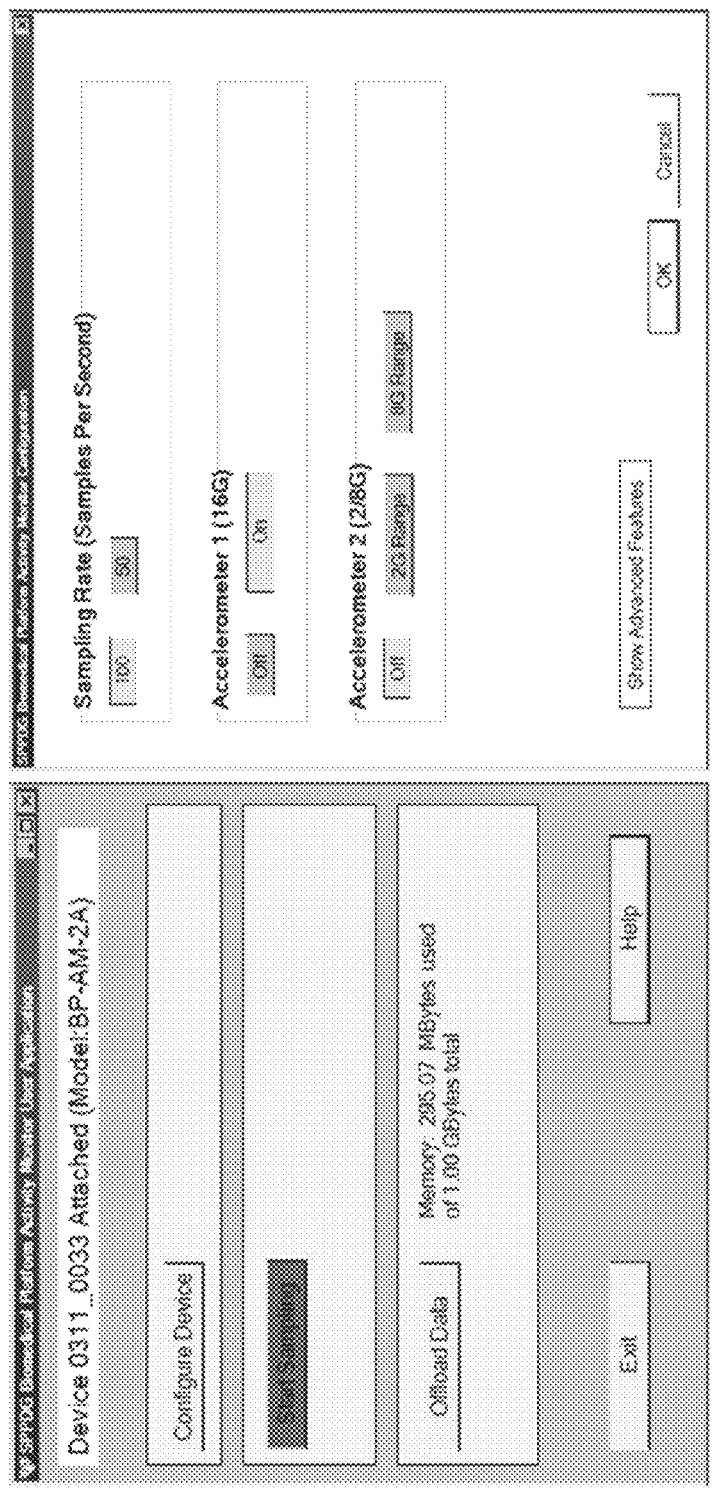
FIG. 20 shows a portion of the interface of the user application with a an embodiment of the monitor that has been operably cooperated with the computer

The left side of FIG. 20 shows a portion of the interface of the user application with a an embodiment of the monitor that has been operably cooperated with the computer. The right side of the figure shows the sensor configuration interface for this embodiment.

Example of an Algorithm Including the ECG Data Processing and Extraction of Heart Rate (HR) and Heart Rate Variability (HRV) Data.

According to an embodiment of the invention, the data processor associated with the monitor of the system is programmed with a computer-readable program product that includes program code enabling the processor to perform at least some of the following data-processing operations:

(1) to convert raw data acquired from a sub-system of the monitor (such as, for example, an ECG circuit 324 of FIG. 3) from unsigned integer values to floating point and scale the so converted data to correspond to a voltage range from the predetermined minimal value (for example, 0 Volts) to a predetermined maximum value (for example, 1 Volt or 2.8 Volts).

(2) to remove the DC voltage baseline from the data.

(3) to take a time-derivative of the resulting data to increase the sensitivity of detection of the R-wave.

(4) to set a threshold and refractory period that are physiologically relevant for the detection of R-waves.

(5) to statistically evaluate the likelihood of the presence, as represented by the data, of a useful R-wave as opposed to an artifact.

(6) to ignore, for the purposes of data processing, time-periods corresponding to the statistically corrupted R-wave measurement based at least in part on extreme amounts of motion at points of predicted artifact.

(7) to map back onto the original signal (represented by the acquired data) the locations of the detected R-waves and, optionally, to display the results of such mapping for the user.

(8) to calculate (and optionally display) a beat-to-beat heart rate (9) to display moving average heart rate parameters.

(10) to estimate (and, optionally, overlay) robust statistical measures of heart rate.

Hardening of an Embodiment for Use in a Harsh Environment.

Of specific interest may be an embodiment that is structured for use by professional mountaineers and climbers in physically harsh environments, for example, during a climb of Mount Everest, while sampling the ECG data at rates of 400 SPS to allow HR and HRV measurements to be made with high precision, and providing a two-week run time to minimize the need to swap devices during the climb. These performance demands, combined with environmental challenges, mandated that extra precautions be taken to insure robustness of the BP-AM-3A. Challenges included making the unit not only wearable and non-irritating for the climbers, but in addition the following accommodations: 1) ruggedness to survive extreme physical activity; 2) coordinated placement of the unit within climber apparel; 3) reduced ECG lead lengths to minimize lead breakage/electrode disconnects; 4) a means for eliminating accidental/undesired activation/deactivations; 5) assurance of electronics and battery survival at reduced operating temperatures (the skin surfaces of climbers in extremely cold environments are typically far less than their core temperatures); 5) unit survival in the face of significant changes in atmospheric pressure; 6) low-humidity environments (creating increased susceptibility to electrostatic discharge (ESD); 7) high humidly environments (due to climber perspiration under layers of clothing); 8) high incidence of gamma rays due to elevation (which can cause single event upsets in the microcontroller); 9) provisions to swap ECG electrodes, ECG leads, and batteries; and 10) the availability of an easily observed visual indicator of proper operation at high ambient light levels.

An aluminum housing was selected (mechanical details and photos are described elsewhere in this document) to provide a mechanically robust and environmentally protective shell, yet be light weight, and provide an ESD shielding cage (Faraday cage) for the electronics. This aluminum shell also provides a minimal shield for gamma rays. The thin case was designed for maximum wearer comfort and to allow the unit to be placed in an appropriately sized apparel pocket centrally located on the chest above the xiphoid process for a tight fit within the pocket and to the body to allow better upper body measurements and for the measurement of smaller thoracic movement during respiratory cycle measurements, and to be in close proximity to the ECG electrodes. This close proximity was intended to minimize ECG lead lengths, which minimizes lead bending and potential breakage, and minimizes physical stresses on the electrodes which in turn minimizes ECG electrode contact resistance.

Even with the aluminum protective shell serving as an ESD shield, an ESD vulnerability may still remain due to the ECG leads as well as vulnerabilities when the units are removed from the wearer and connected to a computer with a USB cable for data offloads, and when batteries are replaced. Accordingly, all inputs and outputs (I/O) including power I/Os were implemented with aggressive ESD protection components, including shunt capacitors and ESD clamp diodes to "case ground" (the term "ground" in this context represents the common electrical point for the embodiment of the monitor, not implying a connection to earth ground). The connection path for these capacitors and diodes had minimal length to insure minimal resistance, and more importantly, minimal inductance. The goal was to provide the absolute lowest possible "ESD event" impedance path from any I/O to the case. The low impedance paths were implemented using multiple copper layers for the connection paths, and included the use of two mechanical screw connections from the circuit board to the case at each of the extreme ends of the circuit board. At one end are the ECG and HDMI connector, while at the other end is the battery replacement access point; both ends require ESD protection. In addition, the ESD ground return path copper plane metallization was isolated from the main PCB ground plane through the use of ferrite chips, which serve as low loss inductors at low frequencies but high impedance series elements for the high frequency ESD transients. The combination of the low impedance shunting (capacitors and diodes) with high impedance series ferrites tend to isolate ESD transients from the sensitive electronics.

The electronic circuits had additional provisions to minimize transient events and electrical disturbances, including multiple capacitors to provide broadband localized decoupling at every electrical component power connection pin.

For example, a small case size (0.02 inches in length) 0.22 uF capacitor was placed as close as possible to the power pin, also to minimize series inductance. This minimal inductance, along with short and direct return paths provide a low impedance path for the highest frequencies. The next capacitor was a medium sized (0.04 inch long) 2.2 uF capacitor exhibiting the next lowest impedance for the mid band frequency decoupling. Next was a large (0.12 inch long) 100 uF capacitor that provided the lower frequency decoupling path. This suite of three capacitors was selected for minimal loss and minimal inductance, and used minimal return path lengths for best decoupling performance. Additional on-PCB shielding and protection was achieved by using multiple power and ground planes. The circuit board incorporates eight metal layers: two are signal, while the remaining six are for power, ground and component attachment on the outer two surfaces. These multiple planes provide lower inductance and increased capacitance (due to the adjacency of the planes), and also shield the sensitive signal layers. Lastly, on all signal and power layers a complete ground ring surrounds the edge of the board, with multiple vias connecting the rings (on each layer) to the multiple ground planes in the board. Thus for the signals there is a shield (board planes and rings) within a shield (outer case), thereby maximizing protection.

Because of the environmental concern regarding humidity, the PCB and all components were coated with a 3M Novec 1700 electronic grade hydrophobic and oleophobic protectant applied to both sides and all edges of the board. In addition, the connector end of the aluminum case was dipped in the moisture protectant, to insure that no wetting surface is present that could allow moisture to condense on the case and or the board at these connector-to-case interfaces. Once the PCB was installed in the case, an additional silicon rubber sealant was used at the connector-to-case interfaces to eliminate any possible gap.

The on/off switch for the unit is a side-activated style that was intentionally recessed to minimize any possibility of accidental activation or deactivation. In addition, a timing loop in the microcontroller requires that the switch be physically activated continuously for two seconds (displayed on the visual LED indicator) for a start or stop to be considered a valid event by the microcontroller software. This switch was positioned at the "top" (connector end) board/case corner to provide convenient user access. The visual indicator is positioned within the other top end corner.

Figure 21:
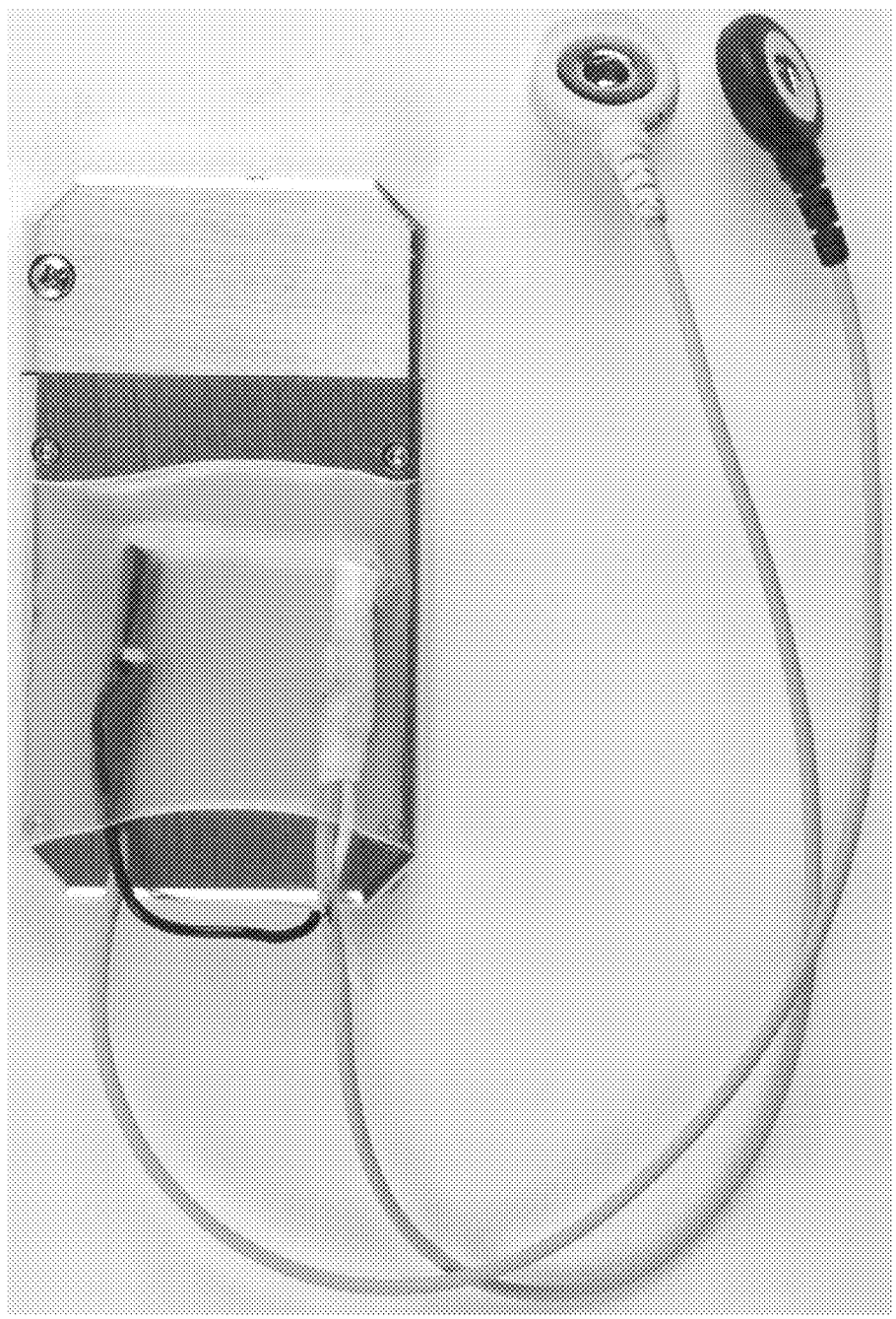
FIG. 21 shows another embodiment of the invention.

To minimize the chance of ECG connector disconnects/strain relief for the climb application, a brute force approach was taken in designing an embodiment of the invention, as depicted in FIG. 21. Small and flexible wires are used from the ECG connector to a strain relief junction. At this junction the small flexible wires are soldered to larger, more robust (yet still flexible) ECG lead wires with ECG snap connectors at the other end for the ECG electrodes. This junction point was triple insulated with heat shrink tubing and the junction was heat shrunk and/or tightly taped to the case, thereby minimizing the possibility that the ECG connector could be pulled out of the case. Care was used to optimize ECG lead positions at the strain relief junction so that when the units were installed in the apparel pocket there would be no lead crossovers.

Figure 22:
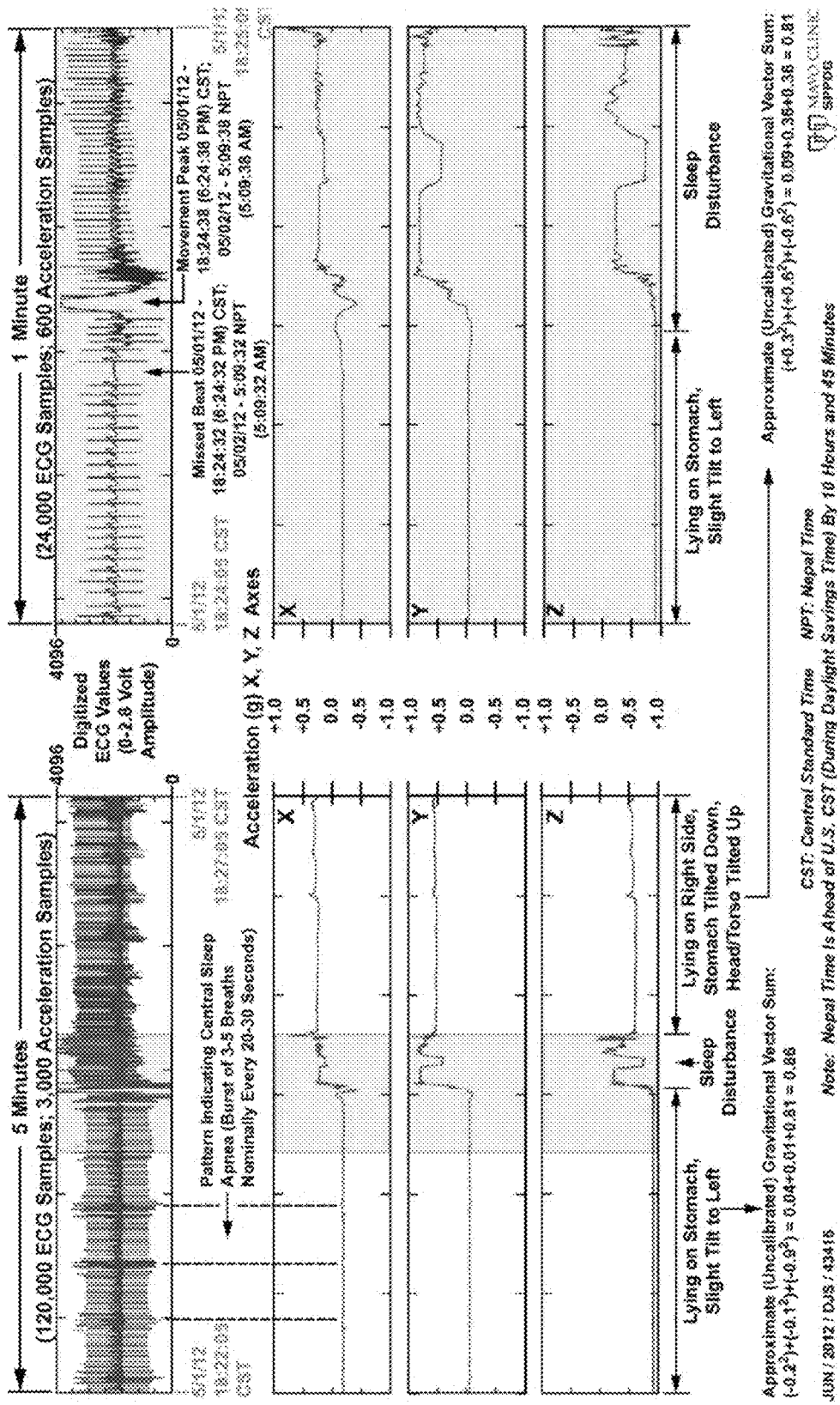
FIG. 22 includes plots of the digitized data representing the ECG activity of a subject under test with an embodiment including a two-electrode configuration of the ECG sensor.

FIGS. 22 through 27 provide illustrations of results of empirical measurements of physiological parameters effectuated with embodiments of the invention that have been juxtaposed with the body of an extreme athlete. FIG. 22 includes plots of the digitized data representing the ECG activity of the athlete 6 (in reference to FIG. 4) with an embodiment including a two-electrode configuration of the ECG sensor configure for operation with at a 400 sample/second rate and an 8 G 3-axes accelerometer configured to operate at a rate of 10 samples/second, with 12 bit resolution. The data were acquired in different orientations of the subject (lying on stomach, sleep disturbance lying on right side).

Figure 23:
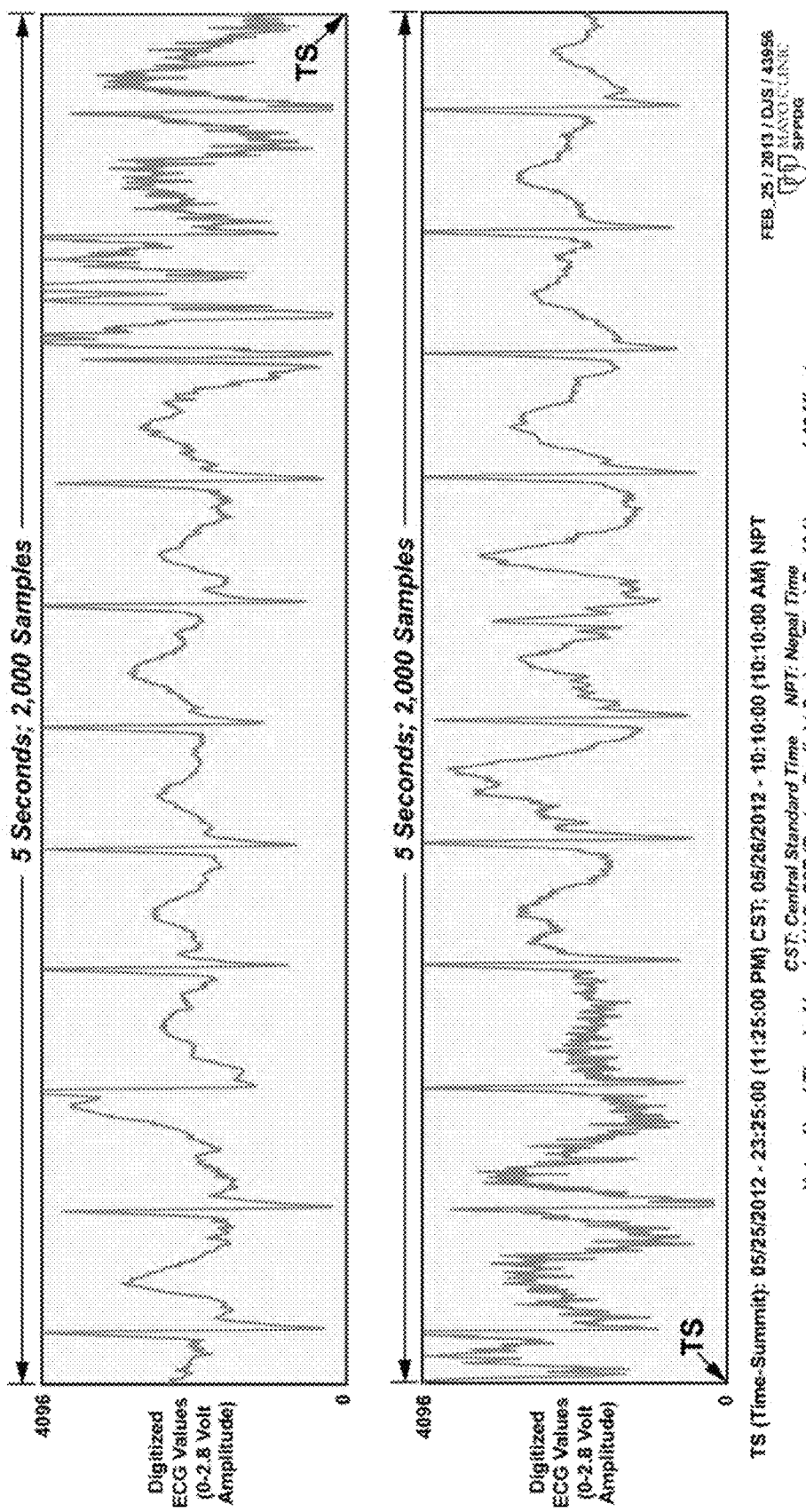
FIG. 23 includes plots representing the results of conversion of raw data acquired from the ECG circuit from unsigned integer values to floating point and scaling the so converted data to correspond to a voltage range from zero volts to 2.8 Volts.

FIG. 23 includes plots representing the results of conversion of raw data acquired from the ECG circuit (used to acquire the data of FIG. 22) from unsigned integer values to floating point and scaling the so converted data to correspond to a voltage range from zero volts to 2.8 Volts (according to an embodiment of the used data-processing algorithm).

Figure 24:
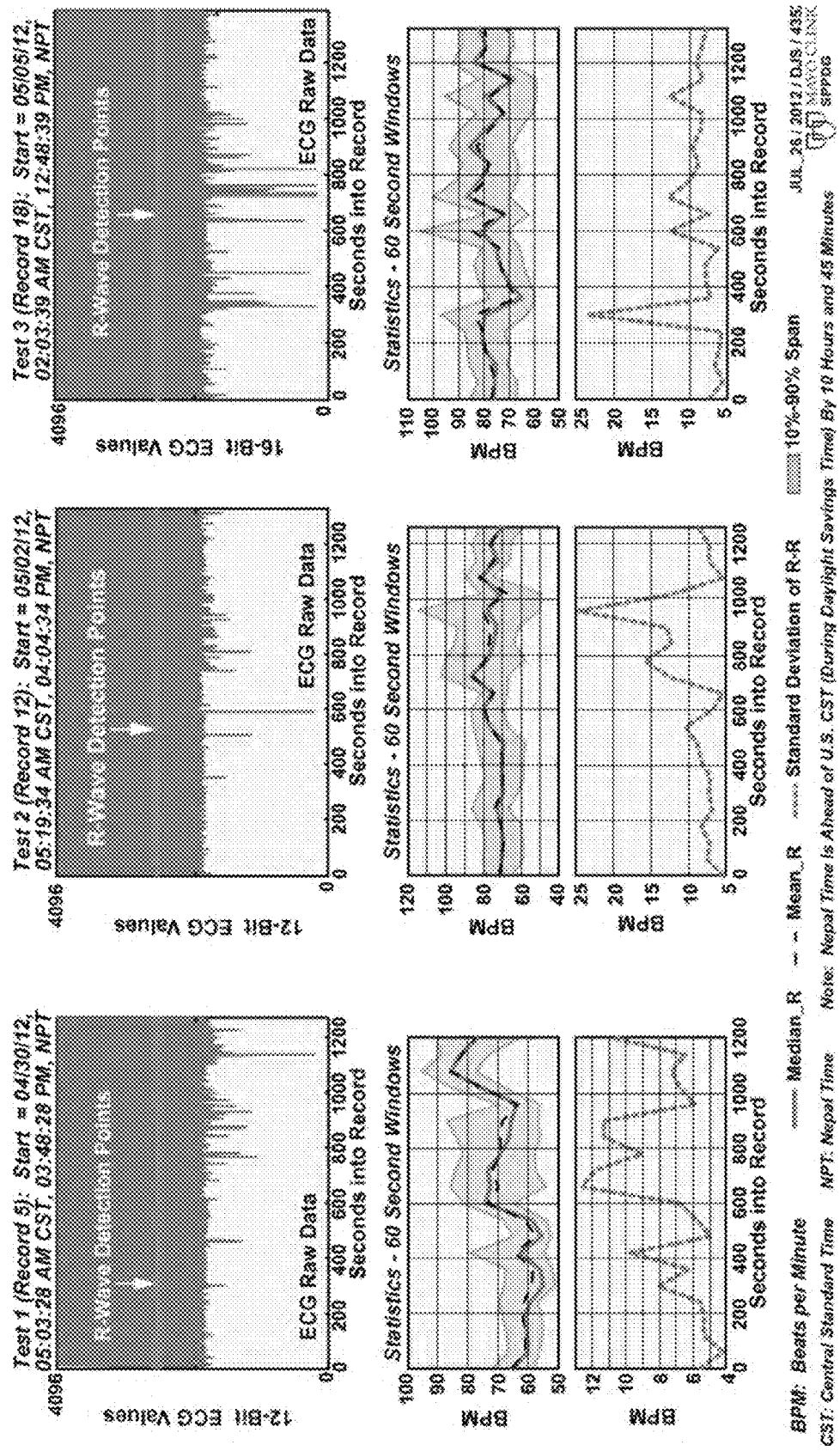
FIG. 24 illustrates samples of the physiological data acquired with the embodiment of the invention, based on which the detection of an R-wave was enabled.

FIG. 24 illustrates samples of the physiological data acquired with the embodiment of the invention, based on which the detection of an R-wave was enabled.

Figure 25:
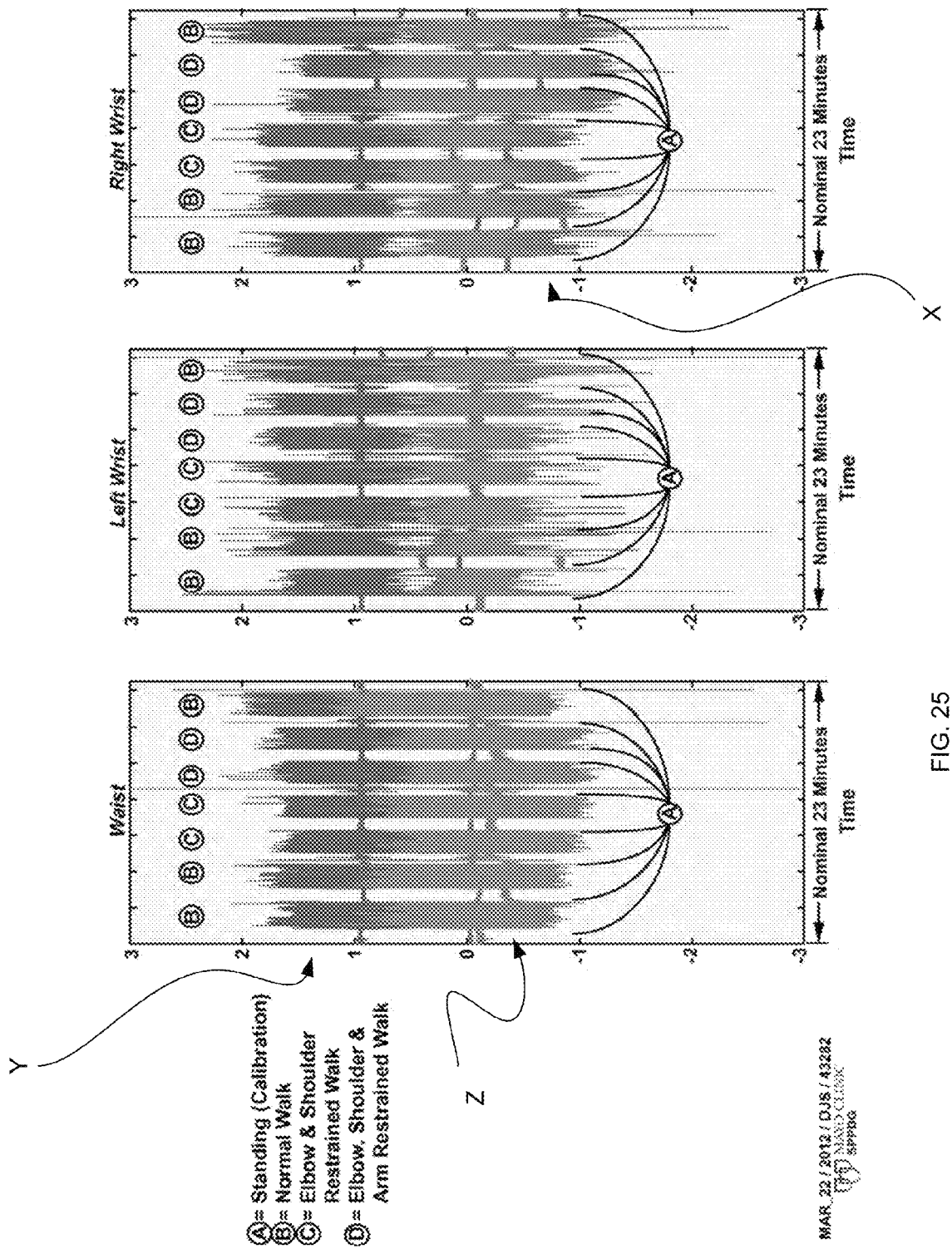
FIG. 25 shows plots representing raw data acquired from a biomedical platform activity monitor of the invention employing a 16 G range accelerometer.

FIG. 25 shows plots representing raw data acquired from a biomedical platform activity monitor of the invention employing a 16 G range accelerometer (312 in FIG. 3) configured to acquire data at 100 sample/second rate with a 12 bit resolution. The embodiment was attached, respectively, to the waist, left wrist, and right wrist of the subject (as shown in FIG. 25). The data are presented without slope and/or offset correction. Here, "X" plot corresponds to data associated with the defined x-axis of orientation, "Y" plot corresponds to data associated with the defined y-axis of orientation, and "Z" plot corresponds to data associated with the defined z-axis of orientation.

Figure 26:
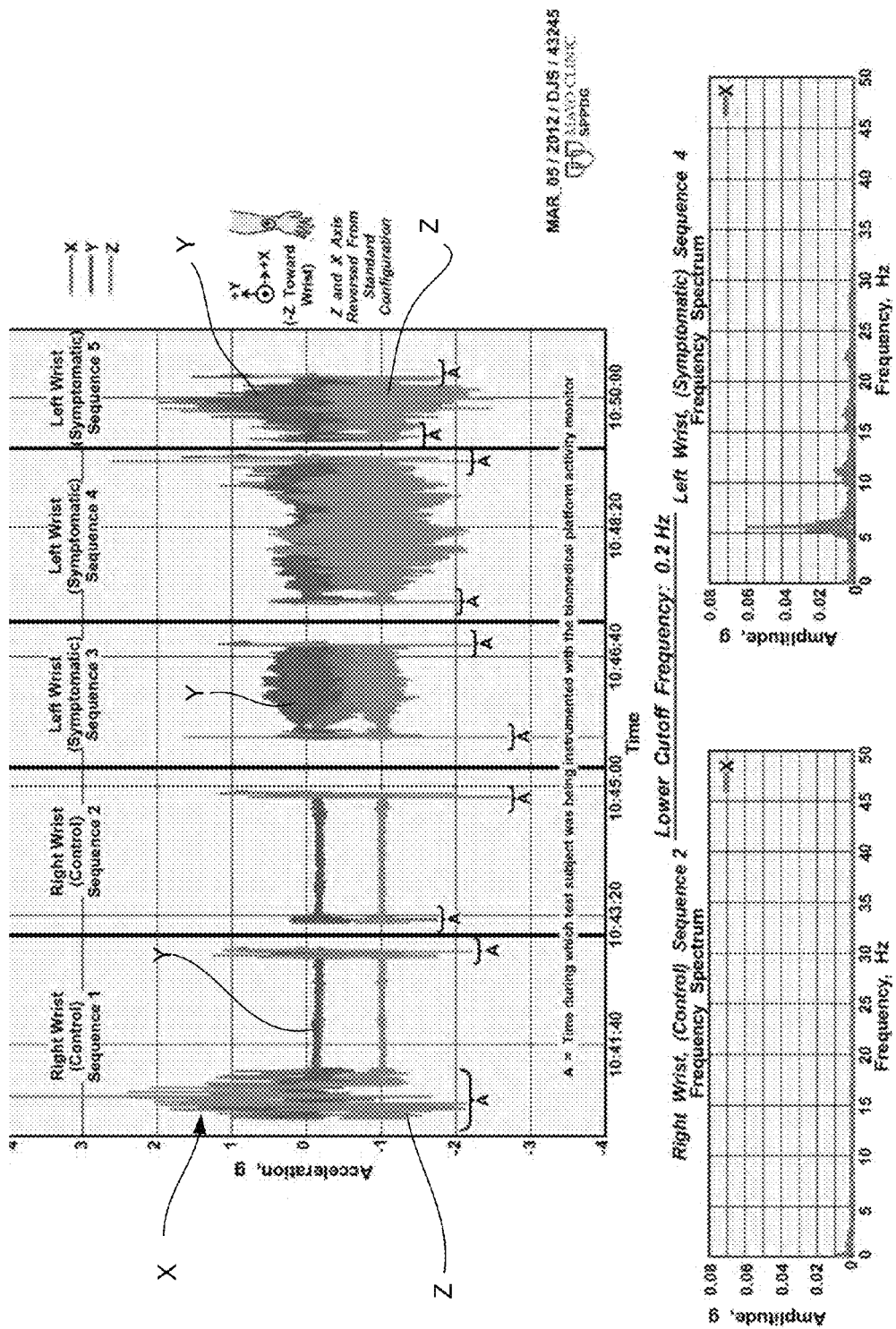
FIG. 26 presents plots describing 16 G raw data acquired from the monitor device of the invention that has been configured to utilize two accelerometers 310, 312 of FIG. 3 for 2 G and 16 G measurements

FIG. 26 presents plots describing 16 G raw data acquired from the monitor of the invention (configured to utilize two accelerometers 310, 312 of FIG. 3 for 2 G and 16 G measurements, respectively at 100 sample/second data acquisitions rate and 12 bit sampling resolution. The bottom portion of FIG. 25 illustrates Fourier spectra of the raw data formed with the data-processing unit of the embodiment.

Figure 27:
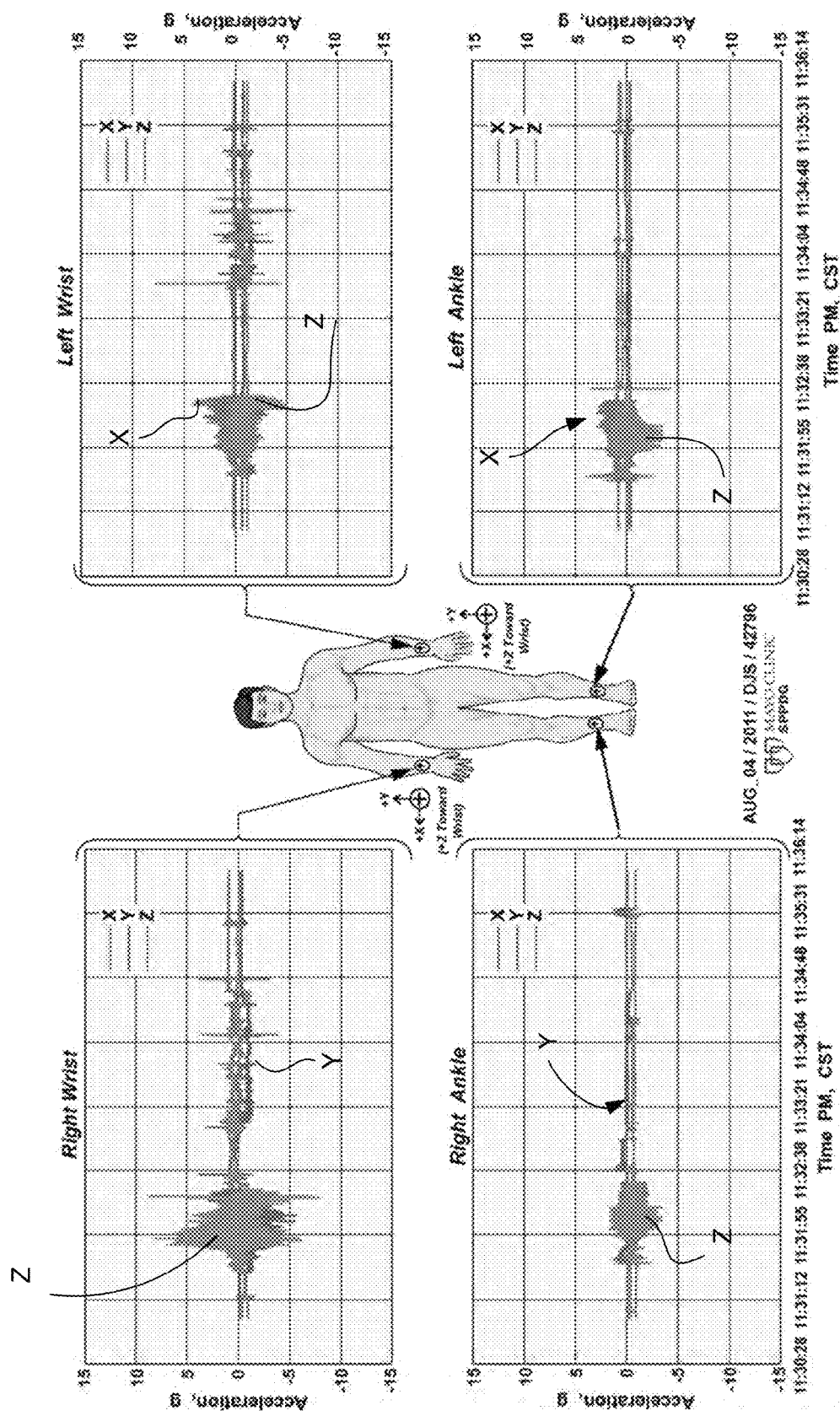
FIG. 27 is a diagram showing the results of measurements (raw data) with an embodiment of the invention juxtaposed, as shown, to the ankles and wrists of an epilepsy subject.

FIG. 27 is a diagram showing the results of measurements (raw data) with an embodiment of the invention juxtaposed, as shown, to the ankles and wrists of an epilepsy subject.

While the invention has been described through the above-presented examples of embodiments, it will be understood by those of ordinary skill in the art that modifications to, and variations of, the illustrated embodiments may be made without departing from the inventive concepts disclosed herein. Furthermore, disclosed aspects, or portions of these aspects, may be combined in ways not listed above. Accordingly, the invention should not be viewed as being limited to the disclosed embodiment(s).

What is claimed is:
1. An article of manufacture, comprising:
a monitor unit including, on a single integrated board,
motion sensors configured to collect first data, representing orientation and motion of the article, simultaneously in multiple ranges of acceleration, wherein a motion sensor is configured to generate a first output,
a physiological sensor enabled to collect second data representing a physiological parameter and generate a second output,
a data-logging unit including tangible non-transitory storage medium,
a controller in operable communication with said motion sensor and the physiological sensor, the controller configured to receive the first and second outputs and route data associated with at least one of the first and second outputs to said data-logging unit,
a clocking device connected to the controller and configured
(i) to produce a time stamp that is associated with a) said received at least one of the first and second outputs and b) synchronization data, and that is configured as a reference for time-alignment of data received from multiple sensors, and (ii) to activate said monitor unit without an input from the user;

and an electrically-conducting lead electrically connected to a port of the monitor unit.

2. An article according to claim 1, wherein the physiological sensor includes an electrocardiographic (ECG) circuit in a two-electrode configuration or a three-electrode configuration, such that said circuit is configured to operate continuously during a two-week period with a nominal current draw of 100 microAmperes and a nominal power consumption of 0.3 mW in said two-electrode configuration or with a nominal current draw of 135 microAmperes and a nominal power of 4 mW in said three-electrode configuration.

3. An article according to claim 1, wherein the motion sensor includes multiple accelerometer units enabling, aggregately and in response to an input applied to the monitor unit, said multiple ranges of acceleration.

4. An article according to claim 1, wherein the motion sensor and the physiological sensor are operable independently from one another, wherein independent operation of the motion sensor and the physiological sensor includes at least one of being powered, having the first and second outputs sampled in frequency, and having the first and second outputs sampled in amplitude.

5. An article according to claim 1, further comprising
a programmable data processor in communication with the data-logging unit,
wherein the physiological sensor includes an electrocardiographic (ECG) circuit, and
wherein said storage medium has computer readable program code disposed therein which causes the programmable data processor
to process raw data acquired from a sensor to form converted data mapped to a range of voltages defined by a predetermined minimum value of voltage and a predetermined maximum value of voltage;
to remove a direct-current voltage baseline from the converted data to form resulting data; and
to calculate a time-derivative of the resulting data to increase sensitivity of detection of an R-wave associated with a subject with the monitor unit that has been juxtaposed to the subject.

6. An article according to claim 5, wherein program code further causes the programmable data processor
to set a threshold and a refractory period, of operation of the monitor unit, that are physiologically relevant to the detection of the R-wave;
to statistically evaluate the likelihood of presence, as represented by the second output, of a useful R-wave as opposed to an artifact; and
to ignore, for the purposes of data processing and based at least in part on extreme amounts of motion at points of predicted artifact, a time-period associated with a measurement and corresponding to a statistically corrupted R-wave.

7. An article according to claim 5, wherein the monitor unit further comprises a transmitter in operable communication with the controller, the transmitter enabled to transmit routing data associated with at least one of the first and second outputs to the programmable data processor.

8. An article according to claim 1, further comprising a display unit in operable communication with the programmable data processor and enabled to form a visually-perceivable representation of a status of at least one of the first and second outputs.

9. An article according to claim 1, further comprising a housing shell defining an inner volume, said housing shell enclosing the monitor unit and dimensioned to allow juxtaposition of the monitor unit with a portion of a body of a wearer of the monitor unit, wherein a motion of arms of the wearer as detected by the motion sensor is minimized, and wherein mechanical interference with clothing of the wearer is minimized.

10. An article according to claim 1, wherein the controller is operably compatible with a multitude of different power battery specifications.

11. An article according to claim 1, wherein the monitor unit further comprises electronic circuitry configured to effectuate at least one of activation and deactivation of the monitor unit in response to a predetermined external event to reduce the amount of at least one of the first and second data.

12. An article according to claim 1, wherein the controller is configured to activate or deactivate the monitor unit only if a switch of the article, once having been physically activated, remains physically activated for a predetermined time interval to generate an indicator of validity of said physical activation of the switch.

13. An article according to claim 1, wherein the physiological sensor includes an oximetry measurement unit configured to effectuate a measurement of one or more of oxygen saturation of a sample tissue, respiration, body temperature, and galvanic skin response.

14. An article according to claim 2, wherein said physiological sensor further comprises a front-end circuit concatenated with said ECG circuit, said front end circuit including
(i) a transceiver and
(ii) a circuit regulator unit configured
to be incorporated into a signal path between said ECG circuit and an antenna of the article when a level of signal received from said ECG circuit by said transceiver falls below a predetermined level, to provide amplification to said signal, and
to be operably by-passed when a level of said signal is above the predetermined level.

15. An article according to claim 1, further comprising a battery to power a component of said article, wherein said port is configured to enable
adjusting of one or more of signal gain and a rate of sampling of the physiological parameter;
downloading of said data received from multiple sensors and said synchronization data;
programming said controller; and
charging said battery.

* * * * *